(12) United States Patent
Antoniou et al.

(10) Patent No.: US 6,797,494 B1
(45) Date of Patent: Sep. 28, 2004

(54) SELF-REPLICATING EPISOMAL EXPRESSION VECTORS CONFERRING TISSUE-SPECIFIC GENE EXPRESSION

(75) Inventors: Michael Antoniou, Edgeware (GB); Frankin G. Grosveld, Rotterdam (NL)

(73) Assignee: Medical Research Council, London (GB)

( * ) Notice: Subject to any disclaimer, the term of this patent is extended or adjusted under 35 U.S.C. 154(b) by 0 days.

(21) Appl. No.: 09/247,054

(22) Filed: Feb. 9, 1999

Related U.S. Application Data

(63) Continuation of application No. PCT/GB97/02213, filed on Aug. 18, 1997, and a continuation of application No. 08/914,715, filed on Aug. 19, 1997, now abandoned
(60) Provisional application No. 60/025,040, filed on Aug. 28, 1996.

(30) Foreign Application Priority Data

Aug. 16, 1996 (GB) ............................................. 9617214

(51) Int. Cl.$^7$ ........................ C12P 21/04; C12N 15/00; C12N 15/09; C12N 15/63; C12N 15/85
(52) U.S. Cl. .................... 435/70.1; 435/320.1; 435/455
(58) Field of Search ............................ 435/70.1, 320.1, 435/455; 514/44; 800/13

(56) References Cited

U.S. PATENT DOCUMENTS 5,674,703 A * 10/1997 Woo et al. .................. 435/69.1
6,022,738 A * 2/2000 Atweh ...................... 435/320.1

FOREIGN PATENT DOCUMENTS

WO    WO 95/33841    12/1995

OTHER PUBLICATIONS

S Safaya et al., Blood, "Augmentation of gamma–Globin Gene Promoter Activity by Carboxylic Acids and Components of the Human beta–Globin Locus Control Region," Dec. 1994, vol. 84, No. 11, pp. 3929–3935.*
GD Elseth, Principles of Modern Genetics, 1994, Chap. 10, pp. 188–189,689,696.*
Chapman et al. Effect of intron A from human cytomegalovirus immediate–early gene on heterologous expression in mammalian cells. Nucl. Acids Res. 19(14): 3979–3986, 1991.*
Greaves et al. Human CD2 3'–flanking sequences confer high–level, T cell–specific, position–independent gene expression in transgenic mice. Cell 56:979–986, Mar. 1989.*
Grosveld et al. Position–independent, high–level expression of the human b–globin gene in transgenic mice. Cell 51: 975–985, Dec. 1987.*

Sadelain et al. Generation of a high–titer retroviral vector capable of expressing high levels of the human b–globin gene. Proc. Natl. Acad. Sci. USA 92: 6728–6732, Jul. 1995.*
Svensson et al. Muscle–based gene therapy: realistic possibilities for the future. Molec. Med. Today 2; 166–172, Apr. 1996.*
Ustav et al. Identification of the origin of replication of bovine papillomavirus and characterization of the viral origin recognition factor E1. EMBO J. 10(13): 4321–4329, 1991.*
Verma et al. Gene therapy—promises, problems, and prospects. Nature 389: 239–242, Sep. 1997.*
Yates et al. Stable replication of plasmids derived from Epstein–Barr virus in various mammalian cells. Nature 313: 812–815, Feb. 1985.*
Wall, RJ Transgenic livestock: Progress and prospects for the future. Theriogenology 45: 57–68, 1996.*
Hammer et al. Spontaneous inflammatory disease in transgenic rats expressing HLA–B27 and human b2m: An animal model of HLA–B27–associated human disorders. Cell 63: 1099–1112, Nov. 1990.*
Mullins et al. Fulminant hypertension in transgenic rats harbouring the mouse Ren–2 gene. Nature 344: 541–544, Apr. 1990.*
Mullins et al. Expression of the DBA/2J Ren–2 gene in the adrenal gland of transgenic mice. EMBO J. 8(13): 4065–4072, 1989.*
Taurog et al. HLA–B27 in inbred and non–inbred transgenic mice. J. of Immunol. 141(11): 4020–4023, Dec. 1988.*
Friedmann et al. Overcoming the obstacles to gene therapy. Sci. Am. Jun. 1997. pp. 96–101, Jun. 1997.*
Orkin and Motulsky. Report and recommendations of the panel to assess the NIH investment in research on gene therapy, Dec. 1995.*
Aleshkov, S.B., et al., "Recombinant Mouse Cell Lines Transformed with Different Type 1 Bovine Papilloma Virus––Based Vectors and Expressing Human Tissues Plasminogen Activator. II. Analysis of Cell Lines Producing Recombinant Tissue Plasminogen Activator," *Molecular Biology*, 1994, 28, 411–414.
PCT International Search Report dated Feb. 24, 1998.
Einerhand, M.P.W., "Regulated High Level Human β–Globin Gene Expression in Erythroid Cells Following Recombinant Adeno–Associated Virus Mediated Gene Transfer", *Gene Therapy*, 1994, 1, p. S2, XP–002055206.

* cited by examiner

*Primary Examiner*—Anne-Marie Falk
(74) *Attorney, Agent, or Firm*—Cozen O'Connor, P.C.

(57) ABSTRACT

Selph-replicating, locus control region (LCR)-containing, episomal expression vectors for tissue-specific gene expression for long-term persistent, tissue-specific expression of a gene of interest are described.

27 Claims, 6 Drawing Sheets

FIG. 1

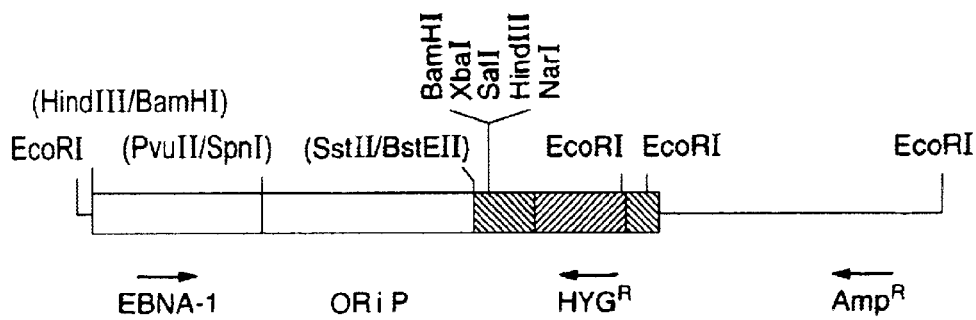

| bp | | |
|---|---|---|
| 1-35 | — | pBR322 |
| 36-2646 | ☐ | EBV EBNA-1 107567-110176 (Baer et. al., Nature 310:1984) Bam HI-PvuII fragment. Bam HI site was blunt-end ligated to the HindIII site. |
| 2647-4826 | ☐ | EBV OriP 7333-9516 SphI-SstII sites blunt-end ligated to the BstEII site. (Sugden et. al., MCB 5:410, 1985) |
| 4827-5460 6488-6747 | ▨ | HSV TK regulatory region (McKnight, S.L., Nucleic Acids Res. 8, 5949, 1980) PvuII fragment ligated into the poisonless pBR322 at NaeI site. These sites lost in cloning. |
| 5461-6487 | ▨ | HPH gene (Gritz and Davies, Gene 25:179, 1983) Bam HI fragment blunt-end ligated into the SmaI and BglII sites in HSV TK sequences. |
| 6748-8952 | — | pBR322 poisonless vector (deletion of 1.1 kb in pBR322) confers ampicillin resistance. (Lusky & Botchan, Nature 293:79, 1981) |

FIG. 4
S1 analysis of K562 cells containing human ß-globin on an EBV based vector
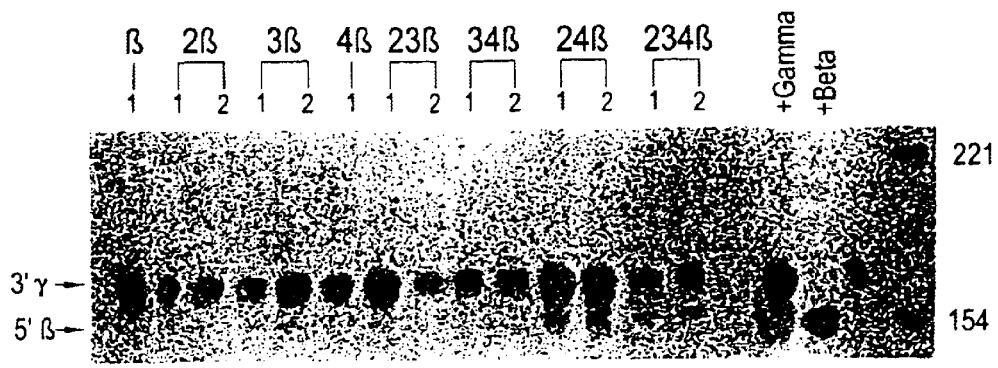
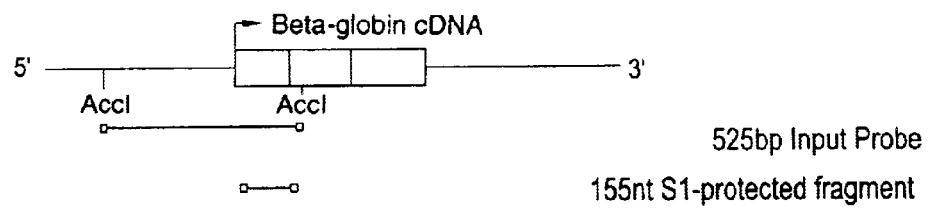
525bp Input Probe
155nt S1-protected fragment
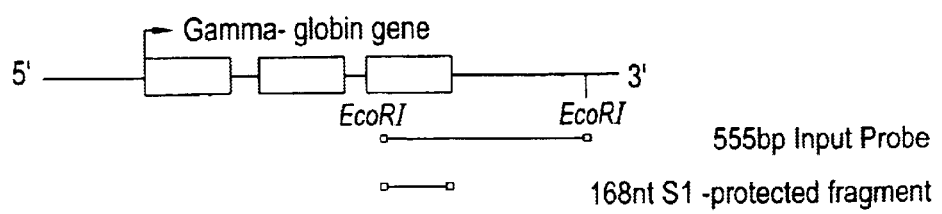
555bp Input Probe
168nt S1-protected fragment

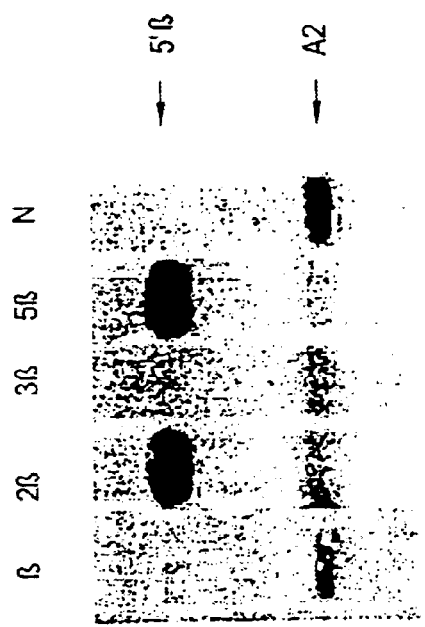
FIG. 5

SEQUENCE LISTING

```
<160> NUMBER OF SEQ ID NOS: 15

<210> SEQ ID NO 1
<211> LENGTH: 12
<212> TYPE: DNA
<213> ORGANISM: Papillomavirus

<400> SEQUENCE: 1
accgttgccg gt                                                          12

<210> SEQ ID NO 2
<211> LENGTH:
<212> TYPE:
<213> ORGANISM:

<400> SEQUENCE: 2

This Sequence is intentionally skipped

<210> SEQ ID NO 3
<211> LENGTH: 31
<212> TYPE: PRT
<213> ORGANISM: Artificial Sequence
<220> FEATURE:
<223> OTHER INFORMATION: Description of Artificial Sequence: Peptide

<400> SEQUENCE: 3

Thr Arg Arg Ala Trp Arg Arg Ala Lys Arg Arg Ala Ala Arg Arg Cys
 1               5                  10                  15

Gly Val Ser Ala Arg Arg Ala Ala Arg Arg Ala Trp Arg Arg Glu
                20                  25                  30

<210> SEQ ID NO 4
<211> LENGTH: 31
<212> TYPE: PRT
<213> ORGANISM: Artificial Sequence
<220> FEATURE:
<223> OTHER INFORMATION: Description of Artificial Sequence: Peptide

<400> SEQUENCE: 4

Thr Lys Lys Ala Trp Lys Lys Ala Glu Lys Lys Ala Ala Lys Lys Cys
 1               5                  10                  15

Gly Val Ser Ala Lys Lys Ala Ala Lys Lys Ala Trp Lys Lys Ala
                20                  25                  30
```

-continued

```
<210> SEQ ID NO 5
<211> LENGTH: 12
<212> TYPE: PRT
<213> ORGANISM: Artificial Sequence
<220> FEATURE:
<221> NAME/KEY: UNSURE
<222> LOCATION: (3)
<223> OTHER INFORMATION: Xaa is Serine, Threonine or Proline
<220> FEATURE:
<221> NAME/KEY: UNSURE
<222> LOCATION: (7)
<223> OTHER INFORMATION: Xaa is Alanine or Valine
<220> FEATURE:
<221> NAME/KEY: UNSURE
<222> LOCATION: (8)
<223> OTHER INFORMATION: Xaa is Alanine, Threonine, or Proline
<220> FEATURE:
<221> NAME/KEY: UNSURE
<222> LOCATION: (9)
<223> OTHER INFORMATION: Xaa is Lysine, Alanine, Threonine or Valine
<220> FEATURE:
<221> NAME/KEY: UNSURE
<222> LOCATION: (12)
<223> OTHER INFORMATION: Xaa is Alanine or Valine
<220> FEATURE:
<223> OTHER INFORMATION: Description of Artificial Sequence: Peptide

<400> SEQUENCE: 5

Lys Lys Xaa Pro Lys Lys Xaa Xaa Xaa Pro Ala Xaa
 1               5                  10

<210> SEQ ID NO 6
<211> LENGTH: 9
<212> TYPE: PRT
<213> ORGANISM: Artificial Sequence
<220> FEATURE:
<221> NAME/KEY: UNSURE
<222> LOCATION: (1)
<223> OTHER INFORMATION: Xaa is Alanine or Valine
<220> FEATURE:
<223> OTHER INFORMATION: Description of Artificial Sequence: Peptide

<400> SEQUENCE: 6

Xaa Lys Ser Pro Ala Lys Ala Lys Ala
 1               5

<210> SEQ ID NO 7
<211> LENGTH: 12
<212> TYPE: PRT
<213> ORGANISM: Artificial Sequence
<220> FEATURE:
<221> NAME/KEY: UNSURE
<222> LOCATION: (1)
<223> OTHER INFORMATION: Xaa is Lysine or Arginine
<220> FEATURE:
<221> NAME/KEY: UNSURE
<222> LOCATION: (2)
<223> OTHER INFORMATION: Xaa is Alanine or Threonine
<220> FEATURE:
<221> NAME/KEY: UNSURE
<222> LOCATION: (10)
<223> OTHER INFORMATION: Xaa is Proline, Alanine or Serine
<220> FEATURE:
<221> NAME/KEY: UNSURE
<222> LOCATION: (12)
<223> OTHER INFORMATION: Xaa is Lysine, Threonine or Valine
<220> FEATURE:
<223> OTHER INFORMATION: Description of Artificial Sequence: Peptide

<400> SEQUENCE: 7

Xaa Xaa Val Lys Pro Lys Ala Ala Lys Xaa Lys Xaa
 1               5                  10
```

```
<210> SEQ ID NO 8
<211> LENGTH: 11
<212> TYPE: PRT
<213> ORGANISM: Artificial Sequence
<220> FEATURE:
<221> NAME/KEY: UNSURE
<222> LOCATION: (1)
<223> OTHER INFORMATION: Xaa is preferably Lysine or Threonine
<220> FEATURE:
<221> NAME/KEY: UNSURE
<222> LOCATION: (2)
<223> OTHER INFORMATION: Xaa is preferably Glysine or Glutamine
<220> FEATURE:
<221> NAME/KEY: UNSURE
<222> LOCATION: (3)
<223> OTHER INFORMATION: Xaa is preferably Glycine, but can also be
      Aspartate, Glutamate, or Serine
<220> FEATURE:
<221> NAME/KEY: UNSURE
<222> LOCATION: (4)
<223> OTHER INFORMATION: Xaa is preferably Glycine, but can also be
      Lysine, Valine, Glutamine, or Threonine
<220> FEATURE:
<221> NAME/KEY: UNSURE
<222> LOCATION: (5)
<223> OTHER INFORMATION: Xaa is preferably Lysine or Alanine
<220> FEATURE:
<221> NAME/KEY: UNSURE
<222> LOCATION: (6)
<223> OTHER INFORMATION: Xaa is preferably Alanine or Lysine
<220> FEATURE:
<221> NAME/KEY: UNSURE
<222> LOCATION: (7)
<223> OTHER INFORMATION: Xaa is preferably Arginine, but can also be
      Valine or Isoleucine
<220> FEATURE:
<221> NAME/KEY: UNSURE
<222> LOCATION: (8)
<223> OTHER INFORMATION: Xaa is preferably Alanine, but can also be
      Threonine, Histidine, or Proline
<220> FEATURE:
<221> NAME/KEY: UNSURE
<222> LOCATION: (9)
<223> OTHER INFORMATION: Xaa is preferably Lysine, Arginine, or
      Glutamine
<220> FEATURE:
<221> NAME/KEY: UNSURE
<222> LOCATION: (10)
<223> OTHER INFORMATION: Xaa is Alanine or Arginine
<220> FEATURE:
<221> NAME/KEY: UNSURE
<222> LOCATION: (11)
<223> OTHER INFORMATION: Xaa is preferably Lysine or Glutamine
<220> FEATURE:
<223> OTHER INFORMATION: Description of Artificial Sequence: Peptide

<400> SEQUENCE: 8

Xaa Xaa Xaa Xaa Xaa Xaa Xaa Xaa Xaa Xaa Xaa
 1               5                  10

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Peptide

<400> SEQUENCE: 9

Lys Gly Gly Gly Lys Ala Arg Ala Lys Ala Lys
 1               5                  10

<210> SEQ ID NO 10
<211> LENGTH: 8
<212> TYPE: PRT
<213> ORGANISM: Artificial Sequence
```

```
<220> FEATURE:
<223> OTHER INFORMATION: Description of Artificial Sequence: Peptide

<400> SEQUENCE: 10

Pro Lys Lys Lys Arg Lys Val Gln
 1               5

<210> SEQ ID NO 11
<211> LENGTH: 61
<212> TYPE: PRT
<213> ORGANISM: Artificial Sequence
<220> FEATURE:
<223> OTHER INFORMATION: Description of Artificial Sequence: Peptide

<400> SEQUENCE: 11

Pro Lys Lys Lys Arg Lys Val Glu Lys Lys Ser Pro Lys Lys Ala Lys
 1               5                  10                  15

Lys Pro Ala Ala Lys Ser Pro Ala Lys Ala Lys Ala Lys Ala Val Lys
             20                  25                  30

Pro Lys Ala Ala Lys Pro Lys Lys Pro Lys Lys Arg Lys Val Glu
         35                  40                  45

Lys Lys Ser Pro Lys Lys Ala Lys Lys Pro Ala Ala Cys
         50                  55                  60

<210> SEQ ID NO 12
<211> LENGTH: 33
<212> TYPE: PRT
<213> ORGANISM: Artificial Sequence
<220> FEATURE:
<223> OTHER INFORMATION: Description of Artificial Sequence: Peptide

<400> SEQUENCE: 12

Lys Ala Val Lys Pro Lys Ala Ala Lys Pro Lys Lys Pro Lys Lys Lys
 1               5                  10                  15

Arg Lys Val Glu Lys Lys Ser Pro Lys Lys Ala Lys Lys Pro Ala Ala
             20                  25                  30

Cys

<210> SEQ ID NO 13
<211> LENGTH: 25
<212> TYPE: PRT
<213> ORGANISM: Artificial Sequence
<220> FEATURE:
<223> OTHER INFORMATION: Description of Artificial Sequence: Peptide

<400> SEQUENCE: 13

Lys Lys Ser Pro Lys Lys Ala Lys Lys Pro Ala Ala Lys Lys Ser Pro
 1               5                  10                  15

Lys Lys Ala Lys Lys Pro Ala Ala Cys
             20                  25

<210> SEQ ID NO 14
<211> LENGTH: 37
<212> TYPE: PRT
<213> ORGANISM: Artificial Sequence
<220> FEATURE:
<223> OTHER INFORMATION: Description of Artificial Sequence: Peptide

<400> SEQUENCE: 14

Lys Lys Ser Pro Lys Lys Ala Lys Lys Pro Ala Ala Lys Lys Ser Pro
 1               5                  10                  15

Lys Lys Ala Lys Lys Pro Ala Ala Lys Lys Ser Pro Lys Lys Ala Lys
             20                  25                  30
```

```
Lys Pro Ala Ala Cys
        35

<210> SEQ ID NO 15
<211> LENGTH: 61
<212> TYPE: PRT
<213> ORGANISM: Artificial Sequence
<220> FEATURE:
<223> OTHER INFORMATION: Description of Artificial Sequence: Peptide

<400> SEQUENCE: 15

Lys Lys Ser Pro Lys Lys Ala Lys Lys Pro Ala Ala Lys Lys Ser Pro
 1               5                  10                  15

Lys Lys Ala Lys Lys Pro Ala Ala Lys Lys Ser Pro Lys Lys Ala Lys
            20                  25                  30

Lys Pro Ala Ala Lys Lys Ser Pro Lys Lys Ala Lys Lys Pro Ala Ala
        35                  40                  45

Lys Lys Ser Pro Lys Lys Ala Lys Lys Pro Ala Ala Cys
    50                  55                  60
```

SELF-REPLICATING EPISOMAL EXPRESSION VECTORS CONFERRING TISSUE-SPECIFIC GENE EXPRESSION

This Application is a continuation of PCT/GB97/02213 filed Aug. 18,1997, which claims priority to GB 9617214.3, and a continuation of application Ser. No. 08/914,715, filed Aug. 19, 1997, now abandoned, which claims priority under 35 U.S.C. § 119(e) to application Ser. No. 60/025,040, filed Aug. 28, 1996, all applications hereby incorporated by reference in their entireties.

FIELD OF THE INVENTION

The invention relates to stable self-replicating episomal expression vectors for expressing a gene of interest in a host cell.

BACKGROUND OF THE INVENTION

The expression of a foreign gene in a host cell is generally achieved by transferring the gene into the host cell using a gene transfer vector. Gene transfer vectors are available in the art and include for example retrovirus vectors, adenoviral vectors and adenoassociated viral vectors. Many transfer vectors operate by integrating at least the transferred gene, if not the complete gene transfer vector, into the host cell chromosome, although non-integrating transfer vectors are known in the art. The efficiency of stable integration of transfected gene constructs is generally very inefficient (1: $10^3$–$10^6$). The disadvantage of using viral vector-based gene transfer is that the amount of genetic material that the vector is able to accommodate is limited by the genetic packaging limitations of the virus. Gene transfer vectors which include large fragments of inserted genetic material are difficult to produce at a sufficiently high titre to be of practical value. Therefore, it is difficult to include additional genetic material in a virus-based vector, for example, gene regulatory elements, without deleteriously affecting stable gene transfer.

Locus Control Regions (LCRs) (Grosveld et al., *Cell* 51:975–985 (1987)), also known as Dominant Activator Sequences, Locus Activating Regions or Dominant Control Regions, confer tissue-specific, integration-site independent copy number-dependent expression on a linked gene that has been integrated into the chromosome of a host cell. LCRs were originally discovered in the human globin gene system, which exhibited strong position effects when integrated into a chromosome of a host cell in a tissue of a transgenic mouse or a mouse erythro-leukaemia (MEL) cell (see, for example, Magram et al., *Nature* 315:338–340 (1985); Townes et al., *EMBO J*. 4:1715–1723 (1985); Kollias et al., *Cell* 46:89–94 (1986); Antoniou et al., *EMBO J*. 7:377–384 (1988)). Position effects were overcome when the LCRs were linked directly to such transgenes (Grosveld et al., supra). Other LCRs have since been identified, including the β-globin LCR (βLCR) which promotes gene expression in erythroid tissue and the CD2 LCR which promotes gene expression in T cells (see, for example, Greaves et al., *Cell* 56:979 (1989), European Patent Application EP-A-0 668 357), themacrophage-specific lysozyme LCR (Boniferet al., (1985, 1990)), and a class II MHC LCR (Carson et al., *Nucleic Acids Res*. 21,9:2065–2072 (1993)).

The present invention provides a stable gene transfer system which, when present in a host cell, confers stable and tissue-restricted expression of a gene of interest carried in the vector.

SUMMARY OF THE INVETNION

This invention provides self-replicating, LCR-containing, episomal expression vectors into which a gene of interest is inserted for expression of the gene in cells of a specific tissue-type.

The invention therefore encompasses a self-replicating episomal DNA expression vector for expressing a gene of interest in a host cell in a tissue-restricted manner, the vector comprising: (a) an origin of replication capable of directing replication of the DNA expression vector in cells of the specific type of tissue; and (b) an LCR, or component thereof, which when operatively linked to a gene of interest and present in a host cell directs expression of the gene in a tissue-restricted manner.

A vector according to the invention also may include the gene of interest inserted into a cloning site and operatively linked to the LCR.

The term gene is used to define any DNA sequence capable of being expressed. The gene of interest may be a foreign or heterologous gene, that is, a gene that is either not normally found in the genomic DNA of the host cell or is not normally expressed in that host cell. The gene of interest also may be an artificial DNA sequence.

The tissue-restricted expression of a gene of interest is mediated in vectors of the invention using an appropriate LCR, or components or portions thereof, which confer tissue-type specific expression on the gene of interest.

As used herein, a locus control region (LCR) is defined as a genetic element which is obtained from a tissue-specific locus of a eukaryotic host cell and which, when linked to a gene of interest and integrated into a chromosome of a host cell, confers tissue-specific, integration-site independent (position independent), copy number-dependent expression on the gene of interest. An LCR that is usefil according to the invention possesses these characteristics when integrated into chromosomal DNA, and will retain the ability to confer tissue-type restricted expression of a linked gene when present in a self-replicating episomal vector according to the invention. A component of an LCR refers to a portion of an LCR that also confers tissue-restricted gene expression when linked to a gene and integrated into a self-replicating episomal vector. An LCR may be identified structurally in that it is associated with one or more DNase I hypersensitive sites in its natural chromosomal context, and a component of an LCR useful according to the invention will also encompass at least one DNase I hypersensitive site.

An enhancer is defined herein as a genetic element which increases the level of transcription of a linked gene when present on a self-replicating episomal vector, but which does not confer tissue-specific gene expression when present on the vector.

It is preferred that the vector comprises a component of an LCR which confers tissue-specific expression and contains at least one DNase I hypersensitive site. In the human β-globin LCR, the preferred component of the LCR consists essentially of HS3; also preferred is the human β-globin LCR excluding site HS2; also preferred are sites HS3 and HS4 together without site HS2.

The invention also encompasses a pair of vectors comprising a self-replicating episomal DNA expression system for expressing a gene of interest in a host cell in a tissue-restricted manner, the pair of vectors comprising: a first vector comprising (a) an origin of replication; (b) an LCR, or component thereof, which when operatively linked to a gene of interest and present in a host cell directs expression of the gene in a tissue-restricted manner; and (c) a cloning site for a gene of interest; and a second vector comprising (d) an origin of replication; and (e) a sequence encoding a replication protein, the replication protein being necessary for replication of the origin of replication.

In another embodiment, the second vector also may include an LCR, which may be the same LCR as is present on the first vector or may be a different LCR which specifies the same or at least an overlapping tissue specificity as the first LCR such that the gene of interest and the viral replication gene are expressed in some of the same cells.

It is preferred that for red cell-restricted gene expression, the β-globin LCR from the β-globin locus be used. As used herein, red cells refer to cells of erythroid lineage.

It is preferred that for T-cell restricted gene expression, the CD2 LCR from the CD2 locus be used, or a component thereofcontaining at least one DNase I hypersensitive site that directs T-cell restricted gene expression in an episomal context. It is preferred that for class II MHC-bearing cell restricted gene expression the class II MHC LCR be used, or a component thereof containing at least one DNase I hypersensitive site that directs MHC-bearing cell restricted gene expression in an episomal context. It also is preferred that for macrophage cell restricted gene expression the macrophage/lysozyme LCR be used, or a component thereof containing at least one DNase I hypersensitive site that directs macrophage-cell restricted gene expression in an episomal context.

The term episomal vector refers to a nucleic acid vector which may be linear or circular, and which is usually double-stranded in form. A vector according to the invention is generally within the size range of 1 kb–1,0000 kb, the preferred size range being on the order of 5 kb–100 kb.

The terms self-replicating, stably maintained and persistence are defined herein as follows. The self-replicating function of a vector of the invention enables the vectors to be stably maintained in cells, independently of genomic DNA replication, and to persist in progeny cells for three or more cell divisions without a significant loss in copy number of the vector in the cells, i.e., without loss of greater than an average of about 50% of the vector molecules in progeny cells between a given cell division. This self-replicating function is provided by using a viral origin of replication and providing one or more viral replication factors that are required for replication mediated by that particular viral origin. Origins of replication and, if necessary, any replication factors may be used from a variety of viruses, including Epstein-Barr virus (EBV), human and bovine papilloma viruses, and papovavirus BK.

In a preferred embodiment, the viral origin of replication is the oriP of EBV and the replication protein factor is the trans-acting EBNA-1 protein. EBNA-1 may be provided by expression of the EBNA-1 gene on the same episomal expression vector carrying OriP or on another vector in the cell or from an EBNA-1 gene in the genomic DNA of the host cell.

In a preferred embodiment, a gene encoding a viral replication factor may be present on the self-replicating episomal vector, i.e., on either the same vector that carries the gene of interest or on another vector of a pair of vectors, and operatively linked to an LCR.

As used herein, linked refers to a cis-linkage in which the gene of interest and/or the gene encoding a viral replication factor and the LCR are contained in the same vector and thus present in cis on the same DNA, and operatively linked refers to a cis linkage in which the gene of interest and/or viral replication gene is subject to tissue-restricted expression via the LCR.

Optionally, a transcription terminator may be introduced into a vector of the invention, preferably between the LCR, or component thereof, and the promoter of the gene of interest or the gene(s) encoding viral replication protein(s) to prevent undesirable transcription of these gene from other promoters that may be present on the vectors. Alternatively, a transcription terminator may be introduced upstream of the LCR and downstream of the gene of interest or viral replication gene(s).

The episomal expression vectors of the invention may be delivered to cells in vivo, ex vivo, or in vitro by any of a variety of the methods employed to deliver DNA molecules to cells. The vectors may also be delivered alone or in the form of a pharmaceutical composition that enhances delivery to cells in the body.

In a preferred embodiment, the vectors ofthis invention are used in gene therapy to express a therapeutically useful protein in the cells of a specific diseased tissue, including tumor tissue, in the body.

Vectors of the invention also are used to express a therapeutically useful protein in cells of a specific tissue-type in vitro.

In another embodiment of this invention, the vectors described herein are used to produce a type of transgenic animal in which a foreign or heterologous gene is expressed only in a specific tissue type, as directed by the LCR, or component thereof, incorporated into the vector. The self-replicating function of the vector ensures that the vector will be passed on to the progeny of the transgenic animal. Such transgenic animals are particularly useful in testing the fidelity and efficacy of tissue-specific gene expression prior to clinical treatment of humans.

In another embodiment of the present invention there is provided a method for identifying an LCR or component thereof which when comprised in an episomal DNA expression vector, operatively linked to a gene of interest and present in a host cell directs expression of said gene in a tissue-restricted manner, comprising:

i. testing the LCR or component thereof by transfecting an episomal vector containing the candidate LCR or component thereof operatively linked to a marker gene into a cell line in which the LCR when integrated is active and also into a cell line in which the LCR when integrated is inactive; and ii. identifying the LCR or component thereof which is only active in the cell line in which the LCR when integrated is active.

Further features and advantages of the invention are found in the following drawings, description and claims.

BRIEF DESCRIPTION OF THE DRAWINGS

FIG. 1 shows a schematic map of an EBV based self-replicating expression vector p220.2. p220.2 is a 8952 bp plasmid which encodes EBNA-1, OriP and hygromycin resistance. It replicates as plasmid in 143 and HeLa cells. EBNA-1 in this construct is driven off an unknown promoter located in the pBR322 sequences. DNA inserted upstream of EBNA-1 appears to eliminate expression of EBNA-1. bp 1–35 are pBR322. bp 36–2646 are EBV EBNA-1 107567–110176 (Baer et al., *Nature.*, 310:207–211, 1984) BamHI-PvuII fragment. The BAMHI site was blunt-end ligated to the HindIII site. bp 2647–4826 are EBV OriP 7333–9516 SphI-SstII sites blunt-end ligated to the BstEII site (Sugden et al., *MCB*, 5:410–413, 1985). bp 4827–5460 are HSV TK regulatory region (McKnight, *NAR*, 8:5949–5964, 1980). bp 6488–6747 are a HSV TK PvuII fragment ligated into poisonless pBR322 at NaeI site. This site is lost in cloning. bp 5461–6487 are the HPH gene (Gritz and Davies, *Gene*, 25:179–188, 1983) BamHI fragment blunt end ligated into the SmaI and BglII sites in HSV TK sequences. bp 6748–8952 are pBR322 poisonless vector (deletion of 1.1 kb in pBR322) confers ampicillin resistance (Lusky & Botchan, *Nature* 293:79–81, 1981). The polylinker form pUC 12 (SmaI-HaeIII fragment) is inserted into a NarI site within the HSV TK sequences. (/) denotes bluntend ligations.

a) the β-globin gene extending from a 5' Hpa I site at −815 bp to an EcoRV site 1685 bp past the poly A addition site in the plasmid GSE1758 (Talbot el aL, *EMBO J*. 9:2169–2178, (1990)) was removed as a 4.1 kb EcoRV fragment and inserted into a blunted SalI site in the polylinker of p220.2 FIG. 1). This cloning step brings a number of extra restriction sites (including a unique SalI site) 5' of the β-globin gene.

Figure 3:
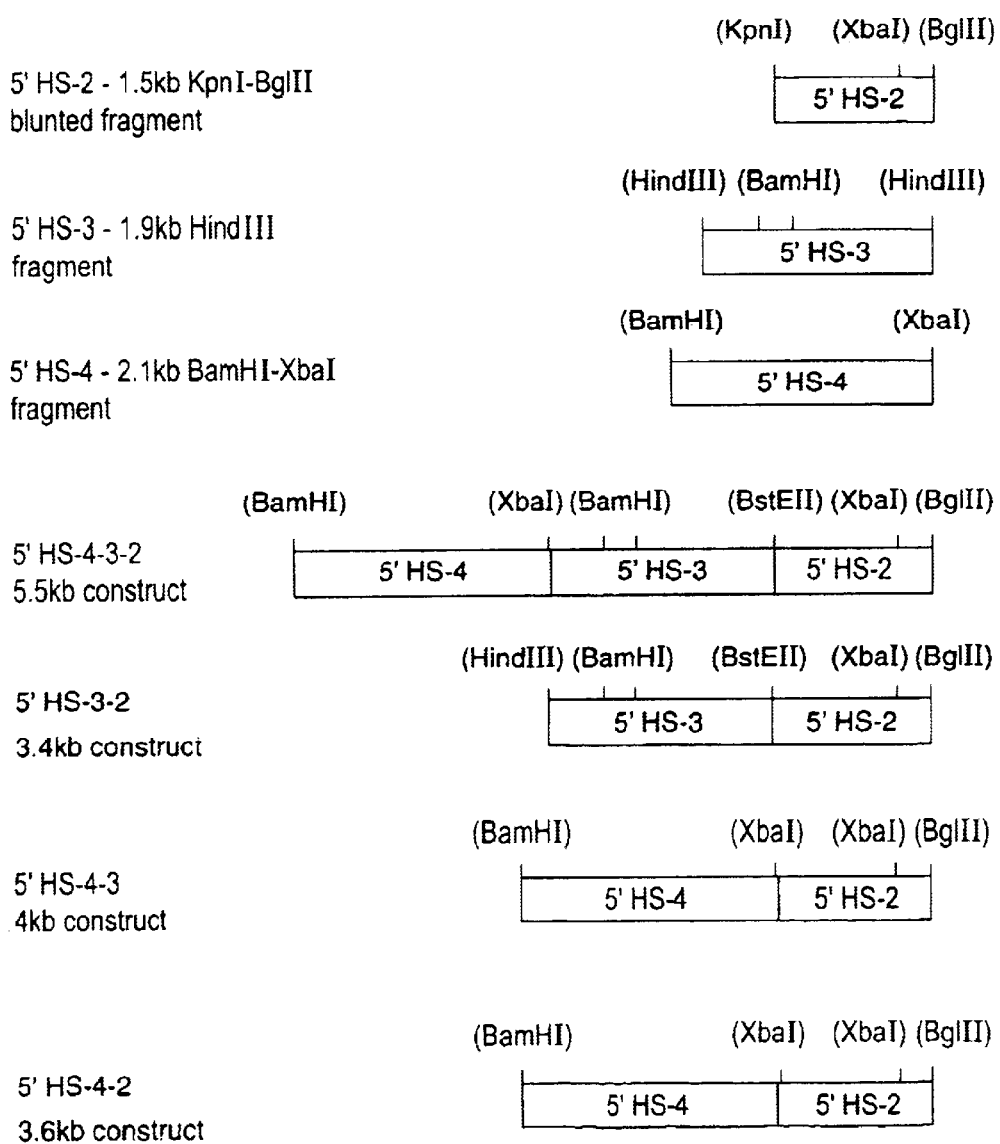

FIG. 3 shows β-Globin LCR Hypersensitive site constructs.

Figure 2:
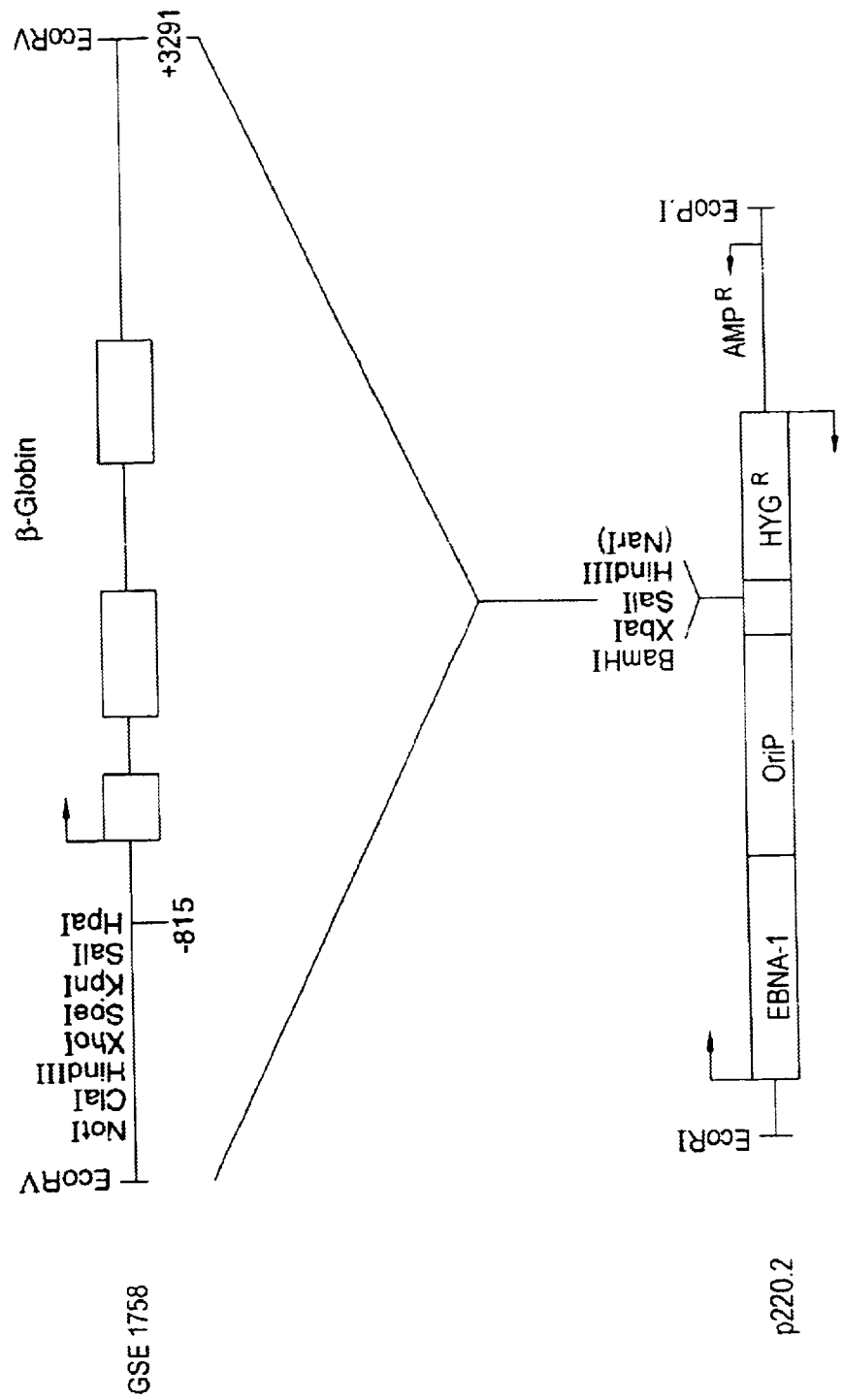
FIG. 2 shows a reporter gene construct.

Constructs which contain more than one hypersensitive site were designed such that the site order matches that of the wild type β-globin locus. SalI linkers were added to both the 5' and 3' ends allowing the DNA to be cloned into the unique SalI site upstream of the β-globin gene in the p220.2 reporter vector (FIG. 2).

FIG. 4 shows:

a) An autoradiogram of an SI nuclease analysis of RNA from K562 cells transfected with self-replicating, episomal, expression vectors containing a human β-globin reporter gene operatively linked to various combinations of HS components from the β-globin LCR. Lane β 1 (β-globin gene alone), lanes 2β 1 and 2 (HS2 operatively linked to β-globin gene), lanes 3β 1 and 2 (HS3 operatively linked to β-globin gene), lanes 4β 1 and 2 (HS4 operatively linked to β-globin gene), lanes 4β 1 and 2 (HS4 operatively linked to β-globin gene), lanes 23β 1 and 2 (HS2/HS3 combination operatively linked to β-globin gene), lanes 34β 1 and 2 (HS3/HS4 combination operatively linked to β-globin gene), lanes 24β 1 and 2 (HS2/HS4 combination operatively linked to β-globin gene), lanes 234β 1 and 2 (HS2/HS3/HS4 combination operatively linked to β-globin gene). Lane +Gamma refers to untransfected K562 cells as a negative control, and lane +beta refers to MEL cells transfected with a β-globin gene +beta βLCR combination which acts as a positive control. All lanes are independent transfections.

b) End labelled DNA probes from the 5'-region of the β-globin gene is shown schematically including the SI protected fragments.

FIGS. 5A and 5B present autoradiograms of RNA blots from K562 or HeLa cells containing constructs described herein. In Panel A: lane M is a HInfl digest of pBR322 size markers; lane P is RNA from MEL cells stably transfected with the human β-globin gene as apositive control; lane β is the human β-globin gene alone; lane 2β is the human β-globin gene under the control of β-globin LCR HS2; lane 3β is the human β-globin gene under the control of β-globin LCR HS3 and lane 5β is the human β-globin gene under the control of β-globin LCR HS2, HS3 and HS4; and lane N is untransfected K562 cells as a negative control. In Panel B, the lanes are the same as indicated for Panel A except lane N is unstransfected HeLa cells as a negative control.

Figure 6:
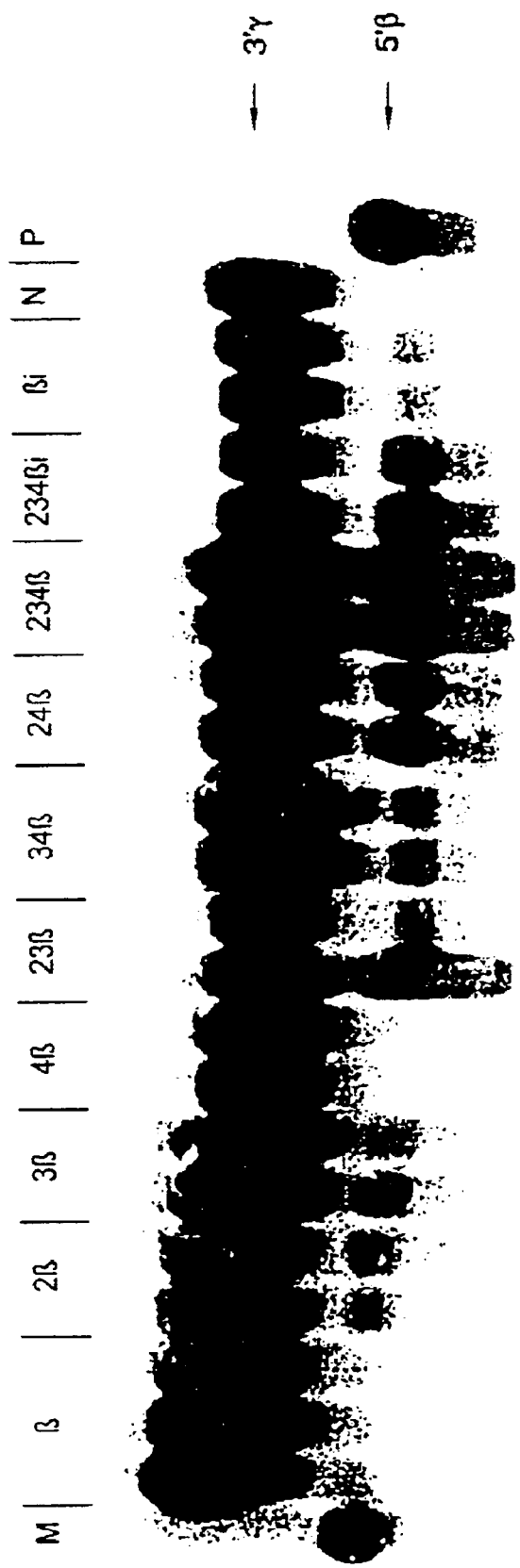

FIG. 6 shows an autoradiogram an SI nuclease analysis of RNA from K562 cells transfected with self-replicating, episomal, expression vectors containing a human β-globin reporter gene operatively linked to various combinations of HS components from the β-globin LCR. Lane M is a marker; lane β is β-globin gene alone; lane 2β is β-globin LCR HS2; lanes 3β are β-globin LCR HS3; lanes 4β are β-globin LCR HS4; lanes 23β are β-globin LCR HS2 and HS3; lanes 34β are β-globin LCR HS3 and HS4; lanes 24β are β-globin LCR HS2 and HS4; lanes 234β are β-globin LCR HS2, HS3 and HS4; lanes 234βi are β-globin LCR HS2, HS3 and HS4 construct as a stable integrant; lanes βi are β-globin gene alone as a stable integrant; lane N is untransfected K562 cells as a negative control; and lane P is untransfected MEL cells stably transfected with the human β-globin gene as a positive control. All lanes are independent transfections.

DETAILED DESCRIPTION OF THE INVENTION

The contents of all references referred to herein are incorporated by reference thereto in their entireties.

The invention is based on the discovery that a locus control region or component thereof may be used in a stable, self-replicating episomal vector containing a gene of interest to specify tissue-restricted expression of the gene of interest.

The stable maintenance of an episomal vector containing an LCR in a host cell is achieved by using an origin of replication that is operative to initiate and replicate an episomal DNA independent of the host cell chromosomes and an origin replication factor.

Origins of Replication and Replication Factors Useful According to the Invention Plasmid vectors for expressing heterologous genes in eukaryotic cells have been made using a portion of the genomic DNA of one or more eukaryotic viruses such as Epstein Barr Virus, human papova virus BK, adenovirus-based vectors, and bovine and human papilloma viruses.

Episomal vectors of the invention comprise a portion of a virus genomic DNA that encodes an origin of replication (ori), which is required for such vectors to be self-replicating and, thus, to persist in a host cell over several generations. In addition, an episomal vector of the invention also may contain one or more genes encoding viral proteins that are required for replication, i.e., replicator protein(s). Optionally, the replicator protein(s) which help initiate replication may be expressed in trans on another DNA molecule, such as on another vector or on the host genomic DNA, in the host cell containing a self-replicating episomal expression vector of this invention.

Preferred self-replicating episomal LCR-containing expression vectors of the invention do not contain viral sequences that are not required for long-term stable maintenance in a eukaryotic host cell such as regions of a viral genome DNA encoding core or capsid proteins that would produce infectious viral particles or viral oncogenic sequences which may be present in the full-length viral genomic DNA molecule.

The term stable maintenance herein, refers to the ability of a self-replicating episomal expression vector of this invention to persist or be maintained in non-dividing cells or in progeny cells of dividing cells in the absence of continuous selection without a significant loss (e.g., >50%) in copy number of the vector for two and preferably five or more generations. The most preferred vectors will be maintained over 10–15 or more cell generations. In contrast, transient or short-term persistence of a plasmid in a host cell refers to the inability of a vector to replicate and segregate in a host cell in a stable manner; that is, the vector will be lost after one or two generations, or will undergo a loss of >51% of its copy number between successive generations.

Several representative self-replicating, LCR-containing, episomal vectors of this invention are described fiuther below. The self-replicating function may alternatively be provided by one or more mammalian sequences such as described by Wohlgemuth et al., 1996, Gene Therapy 3:503; Vos et al., 1995, Jour. Cell. Biol., Supp. 21A, 433; and Sun et al., 1994, Nature Genetics 8:33, optionally in combination with one or more sequence which may be required for nuclear retention. The advantage of using mammalian, especially human sequences for providing the self-replicating function is that no extraneous activation factors are required which could have toxic or oncogenic properties. It will be understood by one of skill in the art that the invention is not limited to any one origin of replication or any one episomal vector, but encompasses the combination of the tissue-restricted control of an LCR in an episomal vector.

1. Epstein-Barr Virus-Based Self-Replicating Episomal Expression Vectors Usefil According to the Invention.

The latent origin oriP from Epstein-Barr Virus (EBV) is described in Yates et. al., *Proc. Natl. Acad. Sci. USA* 81:3806–3810 (1984); Yates et al., *Nature* 313:812–815 (1985); Krysan et al., *Mol. Cell. Biol.* 9:1026–1033 (1989); James et al., *Gene* 86:233–239 (1990), Peterson and Legerski, *Gene* 107:279–284 (1991); and Pan et al., *Som. Cell Molec. Genet.* 18:163–177 (1992)). An EBV-based episomal vector useful according to the invention will contain the orip region of EBV which is carried on a 2.61 kb fragment of EBV (see FIG. 1) and the EBNA-1 gene which is carried on a 2.18 kb fragment of EBV (See FIG. 1). One vector which carries the oriP and EBNA-1 gene of EBV is shown in FIG. 1. The vector shown in FIG. 1 also contains an antibiotic resistance gene for selection of stable transfected eukaryotic cells in culture, a polylinker cloning site for insertion of a gene of interest, and a portion of pBR322 for production of vector DNA in bacterial host cells.

The EBNA-1 protein, which is the only viral gene product required to support in trans episomal replication of vectors containing oriP, may be provided on the same episomal expression vector containing oriP (see, for example, James et al., supra; Peterson and Legerski, supra; Pan et al., supra). It is also understood, that as with any protein such as EBNA-1 known to be required to support replication of viral plasmid in trans, the gene also may be expressed on another DNA molecule, such as a different DNA vector or the host genomic DNA, in the host cell containing the episomal expression vector of the invention.

2. Papilloma Virus-Based, Self-Replicating, Episomal Expression Vectors Useful According to the Invention.

The episomal expression vectors of the invention also may be based on replication functions of the papilloma family of virus, including but not limited to Bovine Papilloma Virus (BPV) and Human Papilloma Viruses (HPVs). BPV and HPVs persist as stably maintained plasmids in mammalian cells. Two trans-acting factors encoded by BPV and HPVs, namely E1 and E2, have also been identified which are necessary and sufficient for mediate replication in many cell types via minimal origin of replication (Ustav et al., *EMBO J.* 10: 449–457 (1991); Ustav et al., *EMBO J.* 10:4231–4329, (1991); Ustav et al., *Proc. Natl. Acad. Sci. USA* 90: 898–902 (1993)).

An episomal vector useful according to the invention is the BPV-1 vector system described in Piirsoo et al., *EMBO J.*, 15:1 (1996) and in WO 94/12629. The BPV-1 vector system described in Piirsoo et al. comprises a plasmid harboring the BPV-1 origin of replication (minimal origin plus extrachromosomal maintenance element) and optionally the E1 and E2 genes. The BPV-1 E1 and E2 genes are required for stable maintenance of a BPV episomal vector. These factors ensure that the plasmid is replicated to a stable copy number of up to thirty copies per cell independent of cell cycle status. The gene construct therefore persists stably in both dividing and non-dividing cells. This allows the maintenance of the gene construct in cells such as hemopoietic stem cells and more committed precursor cells.

The BPV origin of replication has been located at the 3' end of the upstream regulatory region within a 60 base pair (bp) DNA fragment (nucleotides (nt) 7914–7927) which includes binding sites for the E1 and E2 replication factors. The minimal origin of replication of HPV has also been characterized and located in the URR fragment (nt 7022–7927) of HPV (see, for example, Chiang et al., *Proc. Natl. Acad. Sci. USA* 89:5799–5803 (1992)).

As used herein, E1" refers to the protein encoded by nucleotides (nt) 849–2663 of BPV subtype 1 or by nt 832–2779 of HPV of subtype 11, to equivalent E1 proteins of other papilloma viruses, or to functional fragments or mutants of a papilloma virus E1 protein, i.e., fragments or mutants of E1 which possess the replicating properties of E1.

As used herein, E2" refers to the protein encoded by nt 2594–3837 of BPV subtype 1 or by nt 2723–3823 of HPV subtype 11, to equivalent E2 proteins of other papilloma viruses, or to functional fragments or mutants of a papilloma virus E2 protein, i.e., fragments or mutants of E2 which possess the replicating properties of E2.

"Minichromosomal maintenance element" (MME) refers to the extrachromosomal maintenance element of the papilloma viral genome to which viral or human proteins essential for papilloma viral replication bind, which region is essential for stable episomal maintenance of the papilloma viral MO in a host cell, as described in Piirsoo et al. (supra). Preferably, the MME is a sequence containing multiple binding sites for the transcriptional activator E2. The MME in BPV is herein defined as the region of BPV located within the upstream regulatory region which includes a minimum of about six sequential E2 binding sites, and which gives optimum stable maintenance with about ten sequential E2 binding sites. E2 binding site 9 is a preferred sequence for this site, as described hereinbelow, wherein the sequential sites are separated by a spacer of about 4–10 nucleotides, and optimally 6 nucleotides. E1 and E2 can be provided to the plasmid either in cis or in trans, also as described in WO 94/12629 and in Piirsoo et al. (supra).

E2 binding site refers to the minimum sequence of papillomavirus double-stranded DNA to which the E2 protein binds. An E2 binding site may include the sequence 5' ACCGTTGCCGGT 3', SEQ ID NO: 1 which is high affinty E2 binding site 9 of the BPV-1 URR; alternatively, an E2 binding site may include permutations of binding site 9, which permutations are found within the URR, and fall within the generic E2 binding sequence 5' ACCN6GGT 3' SEQ ID NO:2. One or more transcriptional activator E2 binding sites are, in most papillomaviruses, located in the upstream regulatory region, as in BPV and HPV.

A vector which also is useful according to the invention may include a region of BPV between 6959–7945/1–470 on the BPV genetic map (as described in WO 94/12629), which region includes an origin of replication, a first promoter operatively associated with a gene of interest, the BPV E1 gene operatively associated with a second promoter to drive transcription of the E1 gene; and the BPV E2 gene operatively associated with a third promoter to drive transcription of the E2 gene.

E1 and E2 from BPV will replicate vectors containing the BPV origin or the origin of many HPV subtypes (Chiang et al., supra). E1 and E2 from HPV will replicate vectors via the BPV origin and via the origin of many HPV subtypes (Chiang et al., supra). As with all vectors of the invention, the BPV-based episomal expression vectors of the invention must persist through 2–5 or more divisions of the host cell.

3. Papovavirus-Based, Self-Replicating, Episomal Expression Vectors Useful According to the Invention.

The vectors of the invention also may be derived from a human papovavirus BK genomic DNA molecule. For example, the BK viral genome can be digested with restriction enzymes EcoRI and BamHI to produce a S kilobase (kb) fragment that contains the BK viral origin of replication sequences that can confer stable maintenance on vectors (see, for example, De Benedetti and Rhoads, *Nucleic Acids Res.* 19:1925 (1991), as can a 3.2 kb fragment of the BK virus (Cooper and Miron, *Human Gene Therapy* 4:557 (1993)).

4. Regulation of Origin of Replication Factor Expression.

As noted above, the vectors of the invention may contain one or more genes encoding a trans-acting viral replication factor required for stable maintenance of the vectors in host cells.

The regulatory elements, e.g., promoters, enhancers, LCRs, which drive expression of the replicator gene(s) thus may be identical or different, and may provide identical or overlapping tissue-specificity as the LCR, such as, for example, for a tumor that is expressed in B-cells, the immunoglobulin heavy chain promoter/enhancer for B-cells and the Ig heavy or light chain promoters for blood cell expression, or for tumors that are present in an unspecified cell type, and also may include a promoter from a ubiquitously expressed gene, for example from the phosphoglycerolkinase, IE-CMV, RSV-LTR or DHFR genes. The arrangement of replicator gene(s) relative to the episomal vector origin of replication may mimic the natural orientations of these sequences in the virus genome, or it may assume a variety of other orientations, the choices of which will be apparent to one of skill in the art.

In EBV-based episomal vectors, it is often preferable that the transcription of a viral gene encoding a replication factor be placed under the control of a relatively weak promoter. For example, expression of the gene encoding EBNA-1 can be toxic to most cells and/or result in undesirable rearrangements in vector sequences when the gene is expressed using the CMV promoter, a well known, relatively strong, eukaryotic promoter. In contrast, expression of the EBNA-1 gene using a relatively weak eukaryotic promoter sequence permits EBNA-1 to function to maintain a desirable level (i.e., a level that is non-toxic to cells in culture) of vector replication in host cells. Such relatively weak promoter sequences useful in the vectors of the invention are found in a portion of the sequence of the bacterial plasmid pBR322 and the thymidine kinase (tk) promoter.

Preferred promoters for E1 and E2 expression in papillomavirus-based vectors include the thymidine kinase promoter, the SV40 early promoter, the CMV promoter and the SRá promoter 5 Manufacture of Vector DNA.

In another embodiment of the invention, vectors are made comprising culturing a cell containing the vector of the present invention in order to produce sufficient DNA for use according to the invention. It is particularly preferred that such manufacture occurs in lower eukaryotic cells, e.g., yeast or insect, or prokaryotic cells, e.g., bacterial cells such as *E. coli* or Salmonella. Therefore, it is preferred that a vector of this invention will further comprise an origin of replication of yeast, insect or bacterial origin, e.g., the pBR322 origin of replication, and one or more genes encoding a selectable marker, e.g., a gene encoding kanamycin resistance, for selection of cells containing the vector and/or a marker gene such as Lac Z.

LCRs, and Components Thereof, for Providing Tissue-specific Gene Expression Useful According to the Invention The invention contemplates the combination of a stable, self-replicating episomal vector and a locus control region or component thereof for tissue-type restricted expression of a gene contained in the vector.

Without being bound to any one theory, it is believed that, in the genomic DNA context, the LCR promotes an opening of the usually tightly wound structure of the chromatin in cells of a specific tissue type and thereby permits transcription of the genes in the region of the opened chromatin in a tissue-specific manner.

In addition, LCRs are capable of conferring tissue-restricted gene expression whether they are located upstream or downstream of a linked gene, and regardless of orientation with respect to the gene. LCRs useful in an episomal vector according to the invention may be placed upstream or downstream or in any orientation with respect to the linked gene.

Prior to the invention, it was not known whether an LCR, when present in an episomal rather than a chromosomal context, could confer tissue-restricted gene expression. Furthermore, in transient transfections of a vector, LCR components were found not to increase expression levels unless the LCR component comprised a classical enhancer element (Tuan et al., 1989, Proc. Nat. Aca. Sci 86:2544).

In the self-replicating, episomal expression vectors described herein, an LCR, or component thereof, is operatively linked to a selected gene present on the vectors such that the gene expression occurs only in cells of the particular tissue type in which the LCR, or component thereof, is known to function. While not wishing to be limited by a mechanism, it would appear that the self-replicating vectors described herein are stably maintained in a conformation similar to that of the host cell's natural chromatin which the LCR, or component thereof, may be capable of opening and/or then promoting the transcription of sequences to which the LCR, or component thereof, is linked.

In general, whether an LCR or component, or combination of components thereof can be used to mediate tissue specific expression of a foreign gene is easily assayed using a self-replicating episomal vector containing the LCR or component thereof operatively linked to a reporter gene. Expression of the reporter gene in a tissue-specific manner can be assayed using standard methods and by comparing reporter gene expression in cells of the tissue type for which the LCR is specific versus reporter gene expression in cells of a different tissue type. A variety of reporter genes and vectors containing reporter genes are commercially available which can be used for testing promoter and/or enhancer functions. Standard reporter genes used in the art include the lacZ gene encoding β-galactosidase, the CAT gene encoding chloramphenicol acetyl transferase, the luciferase gene system, and the gene encoding alkaline phosphatase (see, for example, James et al., (supra); Peterson and Legerski, (supra); Pan et al., (supra)).

For example, the β-globin LCR contains well-defined portions which are DNA fragments encompassing DNase I hypersensitive sites, i.e., HS1, HS2, HS3, and HS4, located upstream of the fetal globin genes in the β-globin locus; such sites and their detection is described in Tuan et al., supra, 1985). It has been discovered that, when a combination of HS2, HS3, and HS4 components is used in an episomal vector according to the invention, the combination of LCR components containing HS2 does not confer tissue-specific expression of a foreign gene in erythroid cells; similarly, a combination of HS2 and HS3 does not confer tissue-specific expression. However, it also has been discovered the HS3 component alone is effective in conferring tissue specific expression of a linked gene as demonstrated in the Examples below, however, the HS2 component, which is known to be an enhancer, does not possess this activity when present as the sole LCR component on the episomal vector. It is contemplated according to the invention that the absence of HS2 in the episomal β-globin LCR results in tissue-specific gene expression.

Additional LCRs useful according to the invention include but are not limited to the CD2 LCR which promotes gene expression in T cells (see, for example, Greaves et al., (supra)) the macrophage-specific lysozyme LCR (Bonifer et al., (supra)), and a class II MHC LCR (Carson et al., (supra)).

One of skill in the art may, using the benefit of this disclosure, which identifies a β-globin LCR component that confers tissue-specific gene expression when carried on an episome and methods for finding other such LCRs or their components, and techniques available in the art, can identify additional LCRs, or a component thereof, which when carried on an episomal vector confers tissue-specific gene expression.

To identify a component of an LCR that is useful according to the invention (i.e., in an episomal context) one of skill in the art may test each LCR or component thereof (i.e., DNase I hypersensitive site of an LCR) individually by transfecting an episomal vector containing the candidate LCR component and a marker gene into a cell line in which the LCR is active (i.e. active when integrated into the genome (specific cell line)) and also into a cell line in which the LCR is known to be inactive (i.e. inactive when integrated into the genome (non-specific cell line)). If following selection for stable episomes the LCR component is active in the non-specific cell line, i.e. indicating that the LCR component is not tissue specific (such as HS2 of the β-globin LCR), then the LCR component is excluded as a candidate LCR component useful according to the invention. An LCR component which is not active in the non-specific cell line but is active in the specific cell line is useful according to the invention in that it confers tissue specificity in the context of a stable episome. LCR components which are indicated as being useful according to the invention may then be combined and used together to give potentially enhanced levels of tissue specific expression.

Optionally, one or more transcription terminators may also be incorporated into the vectors of the invention to prevent undesirable transcription from other known or latent promoter sequences in the vector which might proceed through (i.e., transcriptional readthrough) the gene whose expression has been placed under the exclusive control of a particular LCR, or component thereof. An example of such a useful transcription terminator is the β-globin terminator, though other eukaryotic transcription terminators also may be used in the vectors described herein. Preferably, the transcription terminator is placed between the LCR, or component thereof, and the promoter of the gene to which the LCR is operatively linked.

Selecting Heterologous or Foreign Genes of Interest

The vectors of the invention are particularly useful in expressing heterologous or foreign genes in cells of a specific tissue-type.

Examples of therapeutic nucleic acid sequences which may be incorporated into an episomal vector include the following. Therapeutically useful nucleic acid sequences include sequences encoding receptors, enzymes, ligands, regulatory factors, and structural proteins. Therapeutic nucleic acid sequences also include sequences encoding nuclear proteins, cytoplasmic proteins, mitochondrial proteins, secreted proteins, plasmalemma-associated proteins, serum proteins, viral antigens, bacterial antigens, protozoal antigens and parasitic antigens. Nucleic acid sequences useful according to the invention also include sequences encoding proteins, lipoproteins, glycoproteins, phosphoproteins and nucleic acid (e.g., RNAs or antisense nucleic acids). Proteins or polypeptides which can be expressed using the episomal vector of the present invention include hormones, growth factors, enzymes, clotting factors, apolipoproteins, receptors, drugs, oncogenes, tumor antigens, tumor suppressors, viral antigens, parasitic antigens and bacterial antigens. Specific examples of these compounds include proinsulin, growth hormone, androgen receptors, insulin-like growth factor I, insulin-like growth factor II, insulin-like growth factor binding proteins, epidermal growth factor TGFα, TGF-β, PDGF, angiogenesis factors (acidic fibroblast growth factor, basic fibroblast growth factor and angiogenin), matrix proteins (Type IV collagen, Type VII collagen, laminin), phenylalanine hydroxylase, tyrosine hydroxylase, oncogenes (ras, fos, myc, erb, src, sis, jun), E6 or E7 transforming sequence, p53 protein, Rb gene product, cytokine receptor, Il-1, IL-6, IL-8, viral capsid protein, and proteins from viral, bacterial and parasitic organisms which can be used to induce an immunologic response, and other proteins of useful significance in the body. The gene which can by incorporated is only limited by the availability of the nucleic acid sequence encoding the protein or polypeptide to be incorporated. One skilled in the art will readily recognize that as more proteins and polypeptides become identified they can be integrated into the episomal vector and expressed in the animal or human tissue.

Vectors of the invention also may be used to express genes that are already expressed in a host cell (i.e., a native or homologous gene), for example, to increase the dosage of the gene product. It should be noted, however, that expression of a homologous gene may result in deregulated expression which may not be subject to control by the LCR, or component thereof, due to its over-expression in the cell.

Vector Delivery

Numerous techniques are known and useful according to the invention for delivering self-replicating, LCR (or component thereof)-containing, episomal expression vectors described herein cells including the use of nucleic acid condensing agents, electroporation, complexation with asbestos, polybrene, DEAE cellulose, Dextran, liposomes, lipopolyamines, polyornithine, particle bombardment and direct microinjection (reviewed by Kucherlapati and Skoultchi, *Crit. Rev. Biochem.* 16:349–379 (1984); Keown et al., *Methods Enzymol.* 185:527 (1990)).

A vector of the invention may be delivered to a host cell non-specifically or specifically (i.e., to a designated subset of host cells) via a viral or non-viral means of delivery.

Preferred delivery methods of viral origin include viral particle-producing packaging cell lines as transfection recipients for the vector of the present invention into which viral packaging signals have been engineered, such as those of adenovirus, herpes viruses and papovaviruses. Preferred non-viral based gene delivery means and methods may also be used in the invention and include nucleic acid condensing peptides, encapsulation in liposomes, and transfection of cells ex vivo with subsequent reimplantation or administration of the transfected cells.

Various peptides derived from the amino acid sequences of viral envelope proteins have been used in gene transfer when co-administered with polylysine DNA complexes (Plank et al., *J. Biol. Chem.* 269:12918–12924 (1994)); Trubetskoy et al., *Bioconjugate Chem.* 3:323–327 (1992); WO 91/17773; WO 92/19287; and Mack et al., *Am. J. Med. Sci.* 307:138–143 (1994)) suggest that co-condensation of polylysine conjugates with cationic lipids can lead to improvement in gene transfer efficiency. PCT publication number WO 95/02698 discloses the use of viral components to attempt to increase the efficiency of cationic lipid gene transfer.

Nucleic acid condensing agents useful in the invention include spermine, spermine derivatives, histones, cationic peptides and polylysine. Spermine derivatives refers to analogues and derivatives of spermine and include compounds as set forth in International Publication No. WO 93/18759 (published Sep. 30, 1993).

Disulfide bonds have been used to link the peptidic components of a delivery vehicle (Cotten et al., *Meth. Enzymol.* 217:618–644 (1992)); see also, Trubetskoy et al. (supra).

Delivery vehicles for delivery of DNA constructs to cells are known in the art and include DNA/poly-cation complexes which are specific for a cell surface receptor, as described in, for example, Wu and Wu, *J. Biol. Chem.* 263:14621 (1988); Wilson et al., *J. Biol. Chem.* 267:963–967 (1992); and U.S. Pat. No. 5,166,320).

Delivery of a vector according to the invention is contemplated using nucleic acid condensing peptides. A nucleic acid condensing peptide which is particularly useful for condensing the nucleic acid construct and therefore for delivering nucleic acid to a cell includes an amino acid sequence of the generic formula

$$NH_2-A-(X_1X_2Y_1Y_2)_nX_3X_4-(Z_1Z_2Z_3Z_4)-(X_5X_6Y_3Y_4)_mX_7X_8BCOOH$$

wherein each of $X_{1-8}$ is, independently, an amino acid having a positively charged group on the side chain; wherein each of $Y_{1-4}$ is, independently, a naturally occurring amino acid which promotes alpha helix formation; wherein each of $Z_{1-4}$ is, independently, a naturally occurring amino acid with at least 3 amino acids having a high propensity to form a stabilized turn structure; wherein A is an amino-terminal serine or threonine residue; wherein B is any amino acid; and wherein n=2–4 and m=2.

Other peptides are those wherein each of $X_{1-8}$ is, independently, lysine, arginine, 2.4-diarnino-butyric acid or ornithine; wherein each of $Y_{1-4}$ is, independently, glutamic acid, alanine, leucine, methionine, glutanine, tryptophan or histidine; wherein each of $Z_{1-4}$ is, independently, asparagine, glycine, proline, serine, and aspartic acid; wherein B is any one of alanine, glutamic acid or cysteine.

It is also contemplated according to the invention that peptides useful in this embodiment of the invention which involves delivery of a nucleic acid to a cell either ex vivo or in vivo may contain one or more internal Serine, Threonine, or Cysteine residues, preferably at a position in the sequence which will be exposed for conjugation to a selected ligand, and thus not on the positively charged (nucleic acid oriented) face of the á-helix. This positioning of selected reactive amino acid residues within the peptide are oriented such that they do not contact the face of the peptide that contacts nucleic acid permits conjugation of the peptide with other functional peptides by bonds of selected and defined stability. Cysteine allows specific conjugation via the thiol side chain to compounds containing other reactive thiol groups (via disulfides), alkylating functions (to form thioether bonds), or other thiol reactive groups such as maleimide derivatives.

Peptides which fall within this generic sequence include:
NBC7
   TRRAWRRAKRRAARRCGVSARRAARRAWRRE-OH; SEQ ID NO: 3 and
NBC11
   H-TKKAWKKAEKKAAKKCGVSAKKAAKKAW KKA-NH₂ SEQ ID NO: 4.

Thus, a nucleic acid condensing peptide useful for delivery of a nucleic acid may contain: 1) helix-forming amino acids, 2) a repeating three-dimensional structure that contacts the major groove of the nucleic acid, 3) suitable chromophores for quantitation, and 4) a number of handles (i.e., reactive sites) for regio-specific conjugation of ligands which form accessory functional domains.

Nucleic acid condensing peptides also may include portions of H1 (sequence I, II or III below) or sequences from other human histones (sequence IV below) which are identified herein as sequences which possess the ability to condense nucleic acid. Therefore, a nucleic acid condensing peptide can include a linear combination of the following three consensus sequences where the total sequence length is >17 residues:

Sequence I: -K-K-X-P-K-K-Y-Z-B-P-A-J- SEQ ID NO: 5
where: K is Lysine, P is Proline; A is Alanine; X is Serine, Threonine or Proline; Y is Alanine or Valine; Z is Alanine, Threonine or Proline; B is Lysine, Alanine, Threonine or Valine; and J. is Alanine or Valine.

Sequence II: -X-K-S-P-A-K-A-K-A- SEQ ID NO: 6
where: X is Alanine or Valine; K is Lysine; S is Serine; P is Proline; and A is Alanine.

Sequence III: -X-Y-V-K-P-K-A-A-K-Z-K-B- SEQ ID NO: 7
where: X is Lysine or Arginine; Y is Alanine or Threonine; Z is Proline, Alanine or Serine; B is Lysine, Threonine or Valine; K is Lysine; P is Proline; A is Alanine.

Sequence IV
   -A-B-C-D-E-F-G-H-I-J-K- SEQ ID NO: 8
where: A is preferably Lysine or Threonine; B is preferably Glycine or Glutamine; C is preferably Glycine, but can also be Aspartate, Glutamnate, or Serine; D is preferably Glycine, but can also be Lysine, Valine, Glutamine, or Threonine; E is preferably Lysine or Alanine; F is preferably Alanine or Lysine, G is preferably Arginine, but can also be Valine or Isoleucine; H is preferably Alanine, but can also be Threonine, Histidine, or Proline; I is preferably Lysine, Arginine, or Glutamine; J is Alanine or Anginine; and K is preferably Lysine or Glutamine. A preferred consensus sequence is:
   -K-G-G-G-K-A-R-A-K-A-K- SEQ ID NO: 9

One such peptide is NBC1, which has the following structure:
   NH₂-[SV40 NLS]-[Seq I]-[Seq II]-[Seq III]-[SV40 NLS]-[Seq I]-C-COOH, where -C- is Cysteine;
where the SV40 NLS has the sequence Pro-Lys-Lys-Lys-Arg-Lys-Val-Gln SEQ ID NO: 10; and the sequence H-PKKKRKVEKKSPKKAKKPAAKSPAKAKAKA
VKPKAAKPKKPKKKRKVEKKSPKKAKKPAAC
(Acm)-OH SEQ ID NO: 11.

Another such nucleic acid condensing peptide of the invention will have an amino acid sequence that falls within the following generic sequence:

$NH_2$-X-(Y)$_n$-C-COOH, where X is either absent or Serine or Threonine; Y is sequence I, II or III as defined above; n is 2–6; and C is Cysteine.

Other such peptides have the following structures and sequences: NBC2 has the structure:

$NH_2$-[Seq III]-[SV40 NLS1]-[Seq I]-C-COOH, where -C- is Cysteine.

NBC8 has the structure: $NH_2$-[Seq I]-[Seq I]-C-COOH, where -C- is Cysteine.

NBC9 has the structure: $NH_2$-[Seq I]-[Seq I]-[Seq I]-C-COOH, where -C- is Cysteine.

NBC10 has the structure: $NH_2$-[Seq I]-[Seq I]-[Seq I]-[Seq I]-C-COOH where -C- is Cysteine; the amino acid sequences of which are as follows:

NBC2 H-KAVKPKAAKPKKPKKKRKVEKKSPKKAK
KPAAC(Acm)-OH SEQ ID NO:12;

NBC8 H-KKSPKKAKKPAAKKSPKKAKK PAAC
(Acm)-OH SEQ ID NO: 13;

NBC9 H-KKSPKKAKKPAAKKSPKKAKKPAAKKSP
KKAKKPAAC(Acm)-OH SEQ ID NO: 14;

NBC10 H-KKSPKKAKKPAAKKSPKKAKKPAAKKSP
KKAKKPAAKKSPKKAKKP AAC(Acm)-OH SEQ
ID NO: 15.

As described above, nucleic acid condensing peptides having a low polydispersion index (PDI) are useful for delivery to a cell of a nucleic acid according to the invention. The PDI for such peptides may be calculated from analysis of the peptides by electro-spray mass spectrometry. This method gives the exact mass of each component to within 0.001%. The PDI values of the peptide preparations useful in the present invention are in the range of 1.0–1.100. Peptide preparations which are especially useful in the invention possess a PDI <1.01, and even <1.001.

The first nucleic acid condensing peptide may include 8–24 positively charged amino acid side groups; for example, the number of positively charged amino acid side groups may be in the range of 12–18.

The ratio of positive/negative charges in a synthetic virus like particle that is capable of targeting a specific mammalian cell type is within the range 0.5–3 per phosphate residue in the nucleic acid; this ratio thus also may be within the range 0.8–1.2.

The ratio of positive/negative charges in a synthetic virus like particle that is unrestricted with respect to the type of cell it targets is in within the range of 0.5–5 per phosphate residue in the nucleic acid, and thus also may be within the range of 1.2–2.

Functional groups may be bound to peptides useful for delivery of a vector according to the invention. These fimctional groups may include a ligand that targets a specific cell-type such as a monoclonal antibody, insulin, transferrin, asialoglycoprotein, or a sugar. The ligand thus may target cells in a non-specific manner or in a specific manner that is restricted with respect to cell type.

The functional group also may comprise a lipid, such as palmitoyl, oleyl, or stearoyl; a neutral hydrophilic polymer such as polyethylene glycol (PEG), or polyvinylpyrrolidine (PVP); a fusogenic peptide such as the HA peptide of influenza virus; or a recombinase or an integrase. The functional group also may comprise an intracellular trafficking protein such as a nuclear localization sequence (NLS).

In a particularly preferred embodiment for delivery, that is, wherein the second functional group is covalently linked to a first functional group which is linked directly to the nucleic acid condensing peptide, the first functional group may comprise one of a lipid or a neutral hydrophilic polymer such as PEG and the second functional group may comprise a ligand that targets a cell surface receptor. For example, when the first functional group comprises a lipid, the second functional group may comprise a ligand that targets a cellular receptor. When the first functional group comprises PEG, the second functional group may comprise a ligand that targets a cellular receptor. The ligand may be, for example, one of a sugar moiety or a ligand whose cellular receptor is restricted to a cell-type, and thus the target cell population may be unrestricted or restricted as to cell type. Alternatively, when the first functional group comprises a lipid, the second functional group may comprise PEG.

The above-described nucleic acid condensing peptide/ vector DNA composition may be prepared as follows. The composition is formulated such that the nucleic acid and the peptide preparation are prepared in equal volumes of the same buffer (usually 0.15M to 1.0M NaCl; 25 mM HEPES, pH 7.4). The nucleic acid is shaken or vortexed while the condensing peptide preparation is added at the rate of 0.1 volume per minute. The complex is left at room temperature for at least 30 minutes prior to addition to the target cells or prior to administration to a subject, and can be stored at 4 C. The particle is centrifuged to remove any aggregated material.

In addition to the above-described DNA/polycation complexes for cell targeting, methods are known in the prior art for preparing cell-targeting liposomes containing nucleic acid. Liposomes are hollow spherical vesicles composed of lipids arranged in a similar fashion as those lipids which make up the cell membrane. They have an internal aqueous space for entrapping water soluble compounds and range in size from 0.05 to several microns in diameter. Several studies have shown that liposomes can deliver nucleic acids to cells and that the nucleic acid remains biologically active.

For example, a liposome delivery vehicle originally designed as a research tool, Lipofectin, has been shown to deliver intact mRNA molecules to cells yielding production of the corresponding protein.

Liposomes offer several advantages: They are non-toxic and biodegradable in composition; they display long circulation half-lives; and recognition molecules can be readily attached to their surface for targeting to tissues. Finally, cost effective manufacture of liposome-based pharmaceuticals, either in a liquid suspension or lyophilized product, has demonstrated the viability of this technology as an acceptable drug delivery system. An example of targeting liposomes is immunoliposomes. Liposomes are prepared, for example, by adsorption of proteins (e.g., inmmunoglobulin) on the liposomal surface; incorporation of native protein into the liposome membrane during its formation (e.g., by ultrasonication, detergent dialysis or reverse phase evaporation); covalent binding (direct or via a spacer group) of a protein to reactive compounds incorporated into the liposomes membrane; noncovalent hydrophobic binding of modified proteins during liposome formation or by the incubation with preformed liposomes); and indirect binding, including covalent binding of immunoglobulin protein via a polymer to the liposome (see Torchilin, V. P. *CRC Critical Reviews in Therapeutic Drug Carrier Systems*, 2(1)). Binding of the nucleic acid-ligand complex to the receptor facilitates uptake of the nucleic acid by receptor-mediated endocytosis.

A nucleic acid-ligand complex linked to adenovirus capsids, which naturally disrupt endosomes, thereby releasing material into the cytoplasm, can be used to avoid degradation of the complex by intracellular lysosomes (see for example Curiel et al., *Proc. Natl. Acad. Sci. USA* 88:8850 (1991); Cristiano et al., *Proc. Natl. Acad. Sci. USA* 90:2122–2126 (1993)). Receptor-mediated nucleic acid uptake can be used to introduce nucleic acid into cells either in vitro or in vivo and, additionally, has the added feature that nucleic acid can be selectively targeted to a particular cell type by use of a ligand which binds to a receptor selectively expressed on a target cell of interest, or can be non-selective with respect to the target cell type.

The precise stoichiometric ratio of the various components of the delivery vehicle can be varied in order to control the magnitude of the initial immune response, the efficiency of delivery and the degree of specific targeting to cells.

In the case of non-specific delivery to cells, a non-specific ligand may be used that targets a cell surface receptor; in the case of specific delivery, a ligand may be used that targets a specific subset of cells. For example, soluble DNA/polylysine complexes can be generated (Li et al., *Biochem. J.* 12:1763 (1973)). Polylysine complexes tagged with asialoglycoprotein have been used to target DNA to hepatocytes in vitro (Wu and Wu, *J. Biol. Chem.* 262:4429 (1987); U.S. Pat. No. 5,166,320). Lactosylated polylysine (Midoux et al., *Nucleic Acids Res.* 21:871–878 (1993)) and galactosylated histones (Chen et al., *Human Gene Therapy* 5:429–435 (1994)) have been used to target plasmid DNA to cells bearing lectin receptors, and insulin conjugated to polylysine (Rosenkrantz et al., *Exp. Cell Res.* 199:323–329 (1992)) to cells bearing insulin receptors. Monoclonal antibodies have been used to target DNA to particular cell types (Machy et al., *Proc. Natl. Acad. Sci. USA* 85:8027–8031 (1988); Trubetskov et al., supra and WO 91/17773 and WO 92/19287).

In a preferred embodiment, a ligand is included in the delivery vehicle for targeting a vector of the invention to cells of a specific type of tissue. Preferably, the ligand is specific for an epitope expressed on the surface of cells of a particular type of tissue. For certain cancer tissue, preferred ligands include antibodies or fragments thereof, such as monoclonal antibody C242 which recognizes the CA242 domain of CanAg expressed on the colon cancers (Lindholm et al., *Int. Arch. Allergy Appl. Immunol.* 71:171–181 (1983) and Larson et al., *Int. J. Cancer* 42:877–882 (1983)); monoclonal antibody SM3, which recognizes polymorphic epythelial mucin (PEM) expressed by breast cancer cells (Burchell et al., *Cancer Research* 47:5476–5482 (1983)) and monoclonal antibodies recognizing a novel epitope found on the epidermal growth factor receptor ofhuman glial tumors but not on normal tissues (Moscatello et al., *Cancer Res.* 55:5536–5539 (1995)). Furthermore, growth factors can also be used to target tumors. For example, the epidermal growth factor (EGF) receptor is over expressed on lung cancer cells and thus EGF can be used as the ligand to target the delivery vehicle to lung cancers (Cristiano et al., *Cancer Gene Therapy* 3:4–10 (1996)).

In addition, certain soluble macromolecules can be used for passive tumor targeting ofcertain tumor types. Many solid tumors possess vasculature that is hyperpermeable to macromolecules. Although the reasons for this are not clearly understood, the result is that such tumors can selectively accumulate circulating macromolecules. The enhanced permeability and retention effect (EPR effect) is thought to constitute the mechanism of action of SMANCS (sytrene/maleic-anhydride-neocarzinostatin), now in regular clinical use in Japan for the treatment of hepatoma. Another class of conjugates under investigation for anticancer activity is N-(2-hydroxypropyl) methacrylamide copolymer-anthracycline conjugates (Seymour, L., *Critical Reviews in Therapeutic Drug Carrier Systems* 9(2):135–187 (1992)). Thus, a polymer comprising styrene/maleic-anhydride or N-(2-hydroxy-propyl)methacrylamide copolymer can be used as a ligand to target the delivery vehicle of the present invention.

Pharmaceutical Compositions and Therapeutic Use

The pharmaceutical compositions of the present invention may comprise a self-replicating episomal vector or delivery composition of the present invention, if desired, in admixture with a pharmaceutically acceptable carrier or diluent, for therapy to treat a disease or provide the cells of a particular tissue with an advantageous protein or function.

A self-replicating episomal, LCR-containing vector of the invention or composition or delivery vehicle comprising a vector of the invention may be administered via a route which includes intramuscular, intravenous, aerosol, oral (tablet or pill form), topical, systemic, ocular, as a suppository, intraperitoneal and/or intrathecal and direct injection of the vector DNA or delivery vehicle into a tumor mass.

The exact dosage regime will, of course, need to be determined by individual clinicians for individual patients and this, in turn, will be controlled by the exact nature of the protein expressed by the gene of interest, and the type of tissue that is being targeted for treatment.

The dosage also will depend upon the disease indication and the route of administration. Advantageously, the vectors of the invention are designed to provide a long-term expression of a selected gene only in the cells of a specific tissue, i.e., in the host cells of tissue in which the LCR, or component thereof, is functional. Thus, in such host cells, duration of treatment will generally be continuous or until the cells die. The number of doses will depend upon the disease, and efficacy data from clinical trials.

The amount of vector DNA delivered for effective gene therapy according to the invention will be in the range of between about 50 ng–1000 $\mu$g of vector DNA/kg body weight; and preferably in the range of between about 1–100 $\mu$g vector DNA/kg.

Although it is preferred according to the invention to administer the episomal vector to a mamnml for in vivo cell uptake, a vector as described herein may be administered utilizing an ex vivo approach whereby cells are removed from an animal, transduced with the episomal vector containing a selected gene under the control of a particular LCR, or component thereof, and then re-implanted into the animal. The liver, for example, can be accessed by an ex vivo approach by removing hepatocytes from an animal, transducing the hepatocytes in vitro with the episomal vector containing a gene encoding a selected protein or therapeutic nucleic acid, and re-implanting the transduced hepatocytes into the animal (e.g., as described for rabbits by Chowdhury et al., *Science* 254:1802–1805, 1991, or in humans by Wilson, *Hum. Gene Ther.* 3:179–222, 1992). Such methods also may be effective for delivering an expression vector of the invention to various populations of cells in the circulatory or lymphatic systems, such as erythrocytes, T cells, and B cells.

Transgenic Animals for Testing Tissue Specificity or Efficacy of Gene Therapy

In another embodiment of the invention, there is provided a mammalian model for determining the tissue-specificity and/or efficacy of gene therapy using a self-replicating episomal LCR-containing vector of the invention. The mammalian model comprises a transgenic animal whose cells contain the vector of the present invention. Methods of making transgenic mice (Gordon et al., *Proc. Natl. Acad. Sci. USA* 77:7380 (1980); Harbers et al., *Nature* 293:540 (1981); Wagner et al., *Proc. Natl. Acad. Sci. USA* 78:5016 (1981); and Wagner et al., *Proc. Natl. Acad. Sci. USA* 78:6376 (1981), sheep, pigs, chickens (see Hammer et al., *Nature* 315:680 (1985)), etc., are well-known in the art and are contemplated for use according to the invention. Such animals permit testing prior to clinical trials in humans.

For example, the transgenic animal may have a tumor or the propensity to develop a tumor. Stewart et al., *Int. J. Cancer* 53:1023 (1993)) describe a transgenic mouse having a T-cell tumor. Teitz et al., *Proc. Natl. Acad. Sci. USA* 90:2910 (1993)) describe transgenic mice having rhabdomyosarcomas and insulin-producing pancreatic-islet tumors. An episomal vector containing a selected gene to be expressed in the tumor cells alone may be transduced into ova from any of these tumor-bearing mice to create an animal model for determining whether the LCR, or component thereof, strictly limits expression of the selected gene to tumor cells and also to determine the result of expressing the selected gene in such tumor cells.

Transgenic animals containing self-replicating, LCR-containing episomal vectors of the invention also may be used for long-term production of a protein of interest in a tissue-specific manner; for example, for production of human globin in red cells of the transgenic animal using the β-globin LCR or the HS 3 and 4 combination or HS3 alone, or production of a protein of interest in milk of a transgenic animal using the LCR macrophage/lysozyme LCR.

The following examples are offered by way of illustration and are not intended to limit the invention in any manner. The preparation, testing and analysis of several representative constructs of the invention is described in detail below. One of skill in the art may adapt these procedures for preparation and testing of other vectors of the invention using different episomal vectors, different LCRs, or components thereof, and different genes of interest.

EXAMPLE 1

Preparation of Test Gene Constructs and Vector Systems

1. EBV Vector

One EBV-based vector useful according to the invention is the p220.2 vector (FIG. 1). The p220.2 vector contains (i) the OriP and EBNA-1 gene from EBV, (ii) a hygromycin resistance gene for selection of stable transfected eukaryotic tissue culture cells, (iii) a polylinker cloning site for test genes and (iv) a pBR322 vector backbone which contains a weak eukaryotic promoter sequence which drives expression of the EBNA-1 gene in eukaryotic cells.

2. Reporter Genes

The reporter genes (FIG. 2) used to assess LCR activity was derived from human β-globin: 4.1 kb HpaI-EcoRV fragment with 815 base pairs (bp) 5' and 1685 bp 3' flanking sequences (Fritsch et al., *Cell* 19:959–972 (1980); Lawn et al., *Cell* 19:959–972 (1980)

The reporter gene was separately cloned by blunt-end ligation into the unique polylinker HindIII site of p220.2 (FIG. 2).

3. β-globin LCR Test Constructs

Three β-globin LCR components are the DNase I hypersensitive sites HS2, HS3 and HS4 (Collis et al., *EMBO J.* 9:223–240 (1990)). These components were cloned as 1.5–2 kb fragments individually or in combinations of two or three sites (see below) upstream of the β-globin or γH2K reporter genes in the SalI site of p220.2 (see, FIG. 3).

EXAMPLE 2

Analysis of Stable Transfection of Tissue Culture Cells

EBV-based vectors are most stable as self-replicating episomes in primate or human cells. Therefore stable transfections of the β-globin LCR test gene constructs were carried out in the human myelogenous leukemia cell line K562 (Lozzio and Lozzio, *Blood* 45:321–334(1975)). This cell line displays an embryonic (â) and foetal (γ) pattern of globin gene expression (Anderson et al., *Int. J. Cancer* 23:143–147 (1979)) and has previously been successfully used to assess β-globin LCR function (Blom van Assendelft et al., *Cell* 56:969–977 (1989)).

1. Transfection Method

K562 cells ($10^7$) were transfected by electroporation with 50 µg of supercoiled test construct DNA using a Bio Rad Gene Pulser (BioRad, Hercules, Calif.) set at 960 µF and 300 V as described in Antoniou, 1991. Each electroporated sample was divided equally between two 75 cm$^2$ tissue culture flasks in order to generate two independent pools of stable transfected cells. Hygromycin B (250 µ/ml) was added 24 hours after electroporation and maintained at this concentration thereafter. Cell death of non-transfected cells was evident after 7–10 days (equivalent to about 10 cell divisions) and confluent flasks of transfected cells were obtained 7 days later.

2. RNA and DNA Preparation from Transfected Cells (i) Total RNA was prepared by selective precipitation in the presence of 3 M LiCl and 6 M urea (Auffrey and Rougeon, *Eur. J. Biochem.* 107:303–314 (1980)).

(ii) Total genomic DNA was prepared from isolated nuclei. Cells (~2×$10^7$) were disrupted in RSB (10 mM Tris-HCl pH 7.5, 10 mM NaCl, 3 mM MgCl$_2$) plus 0.1% NP40 followed by centrifugation to pellet the nuclei. The nuclei were subsequently lysed by resuspending in TNE (150 mM Tris-HCl, pH 7.5, 100 mM NaCl, 5 mM EDTA), 1% SDS and 50 µ/ml proteinase K and incubated overnight at 55 C. This was followed by one extraction with an equal volume of phenol/chloroform (1:1) and the DNA precipitated from the aqueous phase with 0.7 volumes of isopropanol. The resulting DNA precipitate was spooled out of the solution, washed once in 70% ethanol and dissolved in 200 µl of TE (10 mM Tris-Cl. 0.1 mM EDTA, pH 8.0).

3. Analysis for Expression of Test Genes

Transfected gene expression was assessed by an SI-nuclease protection assay (Antoniou et al., *Human Genetic Disease Analysis. A Practical Approach* (second edition) (1993) using an end labeled DNA probe from the 5'-region of the β-globin (Antoniou et al., (1988) or γH2K genes. These probes detect only those transcripts which have arisen by initiation from the correct, wild-type cap site (FIG. 4 and 5, lower panel). As an internal standard, all samples were simultaneously assayed for the endogenous γ-globin mRNA using a probe from the 3'-end of the gene (FIG. 4, lower panel).

4. Assessing Episomal Status and Copy Number of Transfected DNA (a) Episomal Status.

Total DNA (10 µg) from isolated nuclei was digested with Pvu1 and DpnI (6 units) overnight and separated by electrophoresis on a 0.6% agarose gel and Southern blotted onto Magnacharge Plus nylon transfer membranes. DpnI digestion ensures that residual bacterial derived plasmid DNA is destroyed. The blot was then probed with the p220.2 vector labeled with $^{32}$p by nick-translation. Transfected DNA in the form of episomes appear as linear molecules of 12–17.5 kb depending on the size of the test construct.

(b) Episome Copy Number

The same quantity of DNA was digested with EcoRI and DpnI and Southern blotted as above. The blot was probed with an 920 bp BamHI-EcoRI fragment spanning intron II of the β-globin gene. This results in the detection of a 5.5 kb fragment from the three copies of the endogenous β-globin gene and 7.2–12.7 kb fragment from the transfected constructs.

EXAMPLE 3

1. Expression Analysis of β-globin Reported Gene Constructs

FIG. 4 (upper panel) shows the autoradiogram from the analysis of RNA by an S1-nuclease protection assay for the expression of the transfected gene constructs. The sites were linked to the β-globin gene in the EBV-based self-replicating episomal expression vector p220.2 and stably transfected into K562 cells. Total RNA was analyzed by an S1-nuclease protection assay using a mixture of probes to simultaneously detect both the β-globin 5' mRNA from the transgene and the endogenously expressed γ-globin MRNA (3'γ) which acts as an internal reference. Quantitation of the results in FIG. 4 was by Phosphorimager (Molecular Dynamics) and is summarized in Table 1.

In this experiment, little or no expression was seen with the β-globin gene alone (no LCR component present in the self-replicating episomal vector) (lane β1). A vector containing either HS2 or HS4 improved expression only by a small degree (lanes 2β and 4β). In contrast, a vector containing HS3 (lanes 3β) alone gave expression levels that were 10 times greater than a vector containing either HS2 or HS4 alone. The level of expression obtained with a vector containing HS3 was comparable with that observed with a vector containing a combination of HS2/HS3 (lanes 23β) or a vector containing a combination of HS3/HS4 (lanes 34β). The HS2/HS4 vector (lanes 24β) gave the weakest transcriptional activity of the two-site constructs. The highest level of transcription was obtained using a vector containing a combination of all three β-globin LCR elements (HS2,3,4) (lanes 234β). This level was at least twice as great as HS3 alone or the HS2/HS3 and HS3/HS4 two-site constructs.

This experiment was repeated and the results are shown in FIG. 6. The results of this repeated experiment again show that the β-globin gene alone in unable to express in K562 cells (lanes β). The addition of either βOLCR HS2 (lanes 2β) or HS3 (lanes β3), gave significant increases in expression to a comparable degree. HS4 (lanes β4) did not improve expression above that of the β-globin gene alone. The two βLCR HS site combinations (lanes 23β, 34β and 24β)all increased expression above that of any of the HS sites alone. The combination of all 3 HS sites (lanes 234β) gave the highest levels of expression as seen before. The results in FIG. 6 essentially confirm the results shown in FIG. 4, and demonstrate expression with HS2 alone.

TABLE 1

Expression of the human β-globin under the control of the βLCR in self-replicating EBV-based episomal vectors in K562 cells (results shown in FIG. 4).

| Construct | Endogenous/ Exogenous × $10^2$ | Endogenous γ signal | Exogenous β signal |
| --- | --- | --- | --- |
| HS2,3,4β-2 | 32 | 856.338 | 273.22 |
| HS2,3,4β-1 | 28 | 581.853 | 163.35 |
| HS3β-1 | 27 | 309.087 | 84.487 |
| HS3β-2 | 19 | 899.079 | 168.217 |
| HS3,2β-2 | 16 | 342.098 | 55.253 |
| HS4,2β-2 | 15 | 2407.205 | 360.629 |
| HS4,2β-1 | 14 | 2737.317 | 377.922 |
| HS3,2β-1 | 12 | 1181.171 | 143.282 |
| HS4,3β-2 | 9 | 720.397 | 66.132 |
| HS4,3β-1 | 9 | 604.471 | 54.556 |
| β-1 | 7 | 1385.387 | 93.697 |
| HS2β-1 | 6 | 433.451 | 25.151 |
| HS2β-2 | 6 | 421.97 | 24.077 |
| HS4β-1 | 5 | 502.573 | 25.731 |

This table shows the quantitation of the S1 nuclease protection assay shown in FIG. 4, of RNA from K562 cells stably transfected with either the human β-globin gene alone (β-1) or under the control of different combinations of the DNaseI hypersensitive (HS) sites of the βLCR in the self replicating EBV-based vector p220.2 (FIG. 3) using a Molecular Dynamics phosphorimager.

EXAMPLE 4

The human β-globin gene either alone (β) or under the control of βLCR HS2 (2β), HS3 (3β) and HS2, 3 and 4 (5β) in the EBV-based, self-replicating episomal vector p220.2 (see FIGS. 2 and 3), were stably transfected into K562 (Panel A) and HeLa (Panel B) cells by electroporation (see text). Supercoiled plasmid DNA (50 μg) was mixed with 2×10⁷ cells and electroporated with the Bio Rad Gene Pulser set to deliver a single pulse of 960 μF at 300V. Stably transfected cells were selected with 250 μg hygromycin. Total RNA was extracted from the stably transfected pools that were generated and analysed for transgene expression by an S1-nuclease protection assay using end-labelled DNA probes. The β-globin MRNA from the transfected gene was detected with the same 5' probe (5'β) as shown in FIG. 4. Detection of γ-globin mRNA with a 5' exon II probe giving a protected fragment of 207 nucleotides (5'γ), acted as an internal reference in K562 cells. The constitutive and ubiquitously expressed mRNA for hnRNPA2 was probed as an internal reference in the HeLa cell derived samples (giving an 122 nucleotide S1-protected fragment, A2). The results are shown in FIG. 5.

The results show that an episomal vector carrying HS3 alone is expressed tissue-specifically, i.e., in K562 cells but not in HeLa cells, whereas an episomal vector carrying HS2 alone or carrying HS2,3 and 4 is not expressed tissue-specifically, as each is expressed in both K562 and HeLa cells. Therefore, the presence of HS2 in an episomal vector results in expression of the gene of interest but not in a tissue-specific manner, whereas the presence of HS3 alone (i.e, in the absence of HS2) results in expression of the gene of interest in a tissue-specific manner. Therefore, a classical enhancer, such as HS2 (localized to a NF-E2/AP-1 dimer binding site within its core), (Tuan et. al., *Proc. Natl. Acad. Sci. USA* 86:2554–2558 (1989); Ney et. al., *Genes Dev.* 4:993–1006 (1990a); and Ney et al., *Nuc. Acids Res.* 18:6011–6017 (1990b) is distinguishable from an LCR or LCR component specifying tissue-specificity by the inability of the former to confer tissue specific transcription according to the invention.

References

Anderson, L. C., Nilsson, K. And Gahmberg, C. G. (1979) Int. J. Cancer 23, 143–147.
Antoniou, M. (1991) In: Methods in molecular biology: Gene transfer and expression protocols. Murray, E. J. (ed). The Humana Press Inc., Clifton, N.J., pp 421–433.
Antoniou, M. deBoer, E. And Grosveld, F. (1993). In: Human Genetic Disease Analysis. A Practical Approach (second edition) Ed. K. E. Davies, IRL Press, Oxford, 83–108.
Auffrey, C. and Rougeon, F. (1980) Purification of mouse immunoglobulin heavy-chain RNAs from total myeloma tumor RNA. Eur. J. Biochem 107, 303–314
Blom van Assendelfi, M. Hanscombe, O., Grosveld, F. And Greaves, D. R. (1989) Cell 56,969–977.
Collis, P., Antoniou, M. And Grosveld, F. (1990) EMBO J., 9, 223–240.
Fritsche, E. F., Lawn, R. M. and Maniatis, T. (1980) Cell 19, 959–972.
Grosveld, F. Blom van Assendelft, M. Greaves, D. R. and Kollias, G. (1987) Cell 51, 975–958
Lawn, R. M. Efstratiadis, A. O'Connell, C. And Maniatis, T. (1980) Cell 21, 647–651.
Lozzio, C. B. Lozzio, B. B. (1975) Blood 45, 321–334.
Ney, P. A., Sorrentino, B. P., McDonagh, K. T. and Nienhuis, A. W. (1990a) Genes Dev. 4, 993–1006.
Ney, P. A., Sorrentino, B. P., Lowrey, C. H. and Nienhuis, A. W. (1990b) Nucl. Acids Res. 18, 601 1–6017.
Tuan, D. Y. H., Solomon, W. B., London, L. M. and Lee, D. P. (1989) Proc. Natl. Acad. Sci. USA 86, 554–2558.

---

What is claimed is:

1. A vector for expressing DNA comprising:
   a) a self-replicating origin of replication operative in mammalian cells; and
   b) an LCR, or component thereof, which, when operatively linked to a gene of interest and present in a mammalian host cell, directs extrachromosomal transcription of said gene in a tissue-restricted manner, wherein said vector replicates extrachromosomally.

2. A vector for expressing DNA comprising:
   a) a self-replicating origin of replication operative in mammalian cells; and
   b) a β-globin LCR, or component thereof, which, when operatively linked to a gene of interest and present in a mammalian host cell, directs extrachromosomal transcription of said gene in a tissue-restricted manner, wherein said vector replicates extrachromosomally.

3. The vector of claim 2 wherein said vector comprises a component of the β-globin LCR.

4. The vector of claim 3 wherein the component of the β-globin LCR consists essentially of HS3.

5. The vector of claim 3 wherein the component of the β-globin LCR excludes HS2.

6. The vector of claim 3 wherein the component of the β-globin LCR consists essentially of HS3 and HS4.

7. The vector of claim 1, wherein the origin of replication is a viral origin of replication.

8. The vector of claim 7 wherein the viral origin of replication is an origin of replication from Epstein-Barr virus.

9. The vector of claim 1, further comprising a sequence encoding a replication factor required for replication of the expression vector in a host cell.

10. The vector of claim 9 wherein the sequence encoding the replication factor is selected from the group consisting of a sequence encoding EBNA-1 of Epstein-Barr virus, a sequence encoding E1 of papilloma virus, and a sequence encoding E2 of papilloma virus.

11. The vector of claim 1, further comprising an antibiotic resistance gene for selecting cells in culture stably transfected with the vector.

12. The vector of claim 1 or 2, further comprising a gene of interest.

13. The vector of claim 12, further comprising a eukaryotic transcription termination sequence between the LCR and the gene of interest and operative to prevent transcription therebetween.

14. A pair of vectors comprising an expression system for expressing a gene of interest in a host cell in a tissue-restricted manner, the pair of vectors comprising:
   i) a first vector comprising
      (a) a first origin of replication operative in mammalian host cells;
      (b) an LCR, or functional component thereof, which when operatively linked to a gene of interest and present in a mammalian host cell directs extrachromosomal transcription of said gene in a tissue restricted manner; and
      (c) a gene of interest; and
   ii) a second vector comprising
      (a) a second origin of replication operative in a mammalian host cell; and
      (b) a sequence encoding a replication protein, said replication protein being necessary for replication of said second origin of replication, wherein said first and second origins of replication may be the same or different.

15. The pair of vectors of claim 14, wherein the LCR, or component thereof, is a β-globin LCR, or component thereof.

16. The pair of vectors of claim 14 wherein said first vector comprises a component of the β-globin LCR.

17. The pair of vectors of claim 16 wherein said component of the β-globin LCR consists essentially of HS3.

18. The pair of vectors of claim 17 wherein said component of the β-globin LCR excludes HS2.

19. The pair of vectors of claim 17 wherein said component of the β-globin LCR consists essentially of HS3 and HS4.

20. The pair of vectors of claim 14 wherein said origins of replication are viral origins of replication.

21. The pair of vectors of claim 20, said viral origins of replication are from Epstein-Barr virus.

22. The pair of vectors of claim 14 wherein the sequence encoding the replication factor is selected from the group consisting of a sequence encoding EBNA-1 of Epstein-Barr virus, a sequence encoding E1 of papilloma virus, and a sequence encoding E2 of papilloma virus, and a sequence encoding E2 of papilloma virus.

23. The pair of vectors of claim 14, wherein each of said first and second vector further comprises an antibiotic resistance gene for selecting cells in culture stably transfected with the expression vector.

24. The pair of vectors of claim 14 wherein said first vector further comprises a eukaryotic transcription termination sequence placed between the LCR and the gene of interest.

25. A method of obtaining persistent, tissue-specific expression of a gene of interest in a host cell in culture, comprising culturing a host cell transfected with the vector of claim 12.

26. A method of obtaining persistent, tissue-specific expression of a gene of interest in a host cell in culture, comprising culturing a host cell transfected with the pair of vectors of claim 14.

27. A method of identifying an LCR or component thereof which when comprised in a non-integrating DNA expression vector, operatively linked to a gene of interest, and present in a host cell, directs expression of said gene in a tissue-restricted manner, comprising:
  i. testing the LCR or component thereof by transfecting a non-integrating vector containing the candidate LCR or component thereof operatively linked to a maker gene into a cell line in which the LCR when integrated is active and also into a cell line in which the LCR when integrated is inactive; and
  ii. identifying the LCR or component which is only active in the cell line in which the LCR when intergrated is active.

* * * * *